(12) United States Patent
Ryan et al.

(10) Patent No.: US 11,439,313 B2
(45) Date of Patent: Sep. 13, 2022

(54) SMALL FORM FACTOR DIGITALLY TUNABLE NMR IN VIVO BIOMETRIC MONITOR FOR METABOLIC STATE OF A SAMPLE

(71) Applicant: Bitome, Inc., Boston, MA (US)

(72) Inventors: Herbert B. Ryan, Boston, MA (US); Jens Peter Höfflin, Baden-Württemberg (DE); Trevor H. Kemp, Front Royal, VA (US)

(73) Assignee: BITOME, INC., Boston, MA (US)

( * ) Notice: Subject to any disclaimer, the term of this patent is extended or adjusted under 35 U.S.C. 154(b) by 896 days.

(21) Appl. No.: 15/597,053

(22) Filed: May 16, 2017

(65) Prior Publication Data

US 2017/0325710 A1 Nov. 16, 2017

Related U.S. Application Data

(60) Provisional application No. 62/336,887, filed on May 16, 2016.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4875* (2013.01); *A61B 5/6826* (2013.01);
(Continued)

(58) Field of Classification Search
CPC ........ A61B 2503/10; A61B 2560/0431; A61B 5/055; A61B 5/4875; A61B 5/6824;
(Continued)

(56) References Cited

U.S. PATENT DOCUMENTS

| | | | | |
|---|---|---|---|---|
| 2003/0006771 A1* | 1/2003 | Goto | ................... | G01R 33/389 324/309 |
| 2004/0014236 A1* | 1/2004 | Albo | ................... | G01R 33/389 436/173 |

(Continued)

OTHER PUBLICATIONS

Terada et al., Magnetic field shimming of a permanent magnet using a combination of pieces of permanent magnets and a single-channel shim coil for skeletal age assessment of children, May 2013 (Year: 2013).*

(Continued)

*Primary Examiner* — Serkan Akar
(74) *Attorney, Agent, or Firm* — Resolute Legal PLLC

(57) ABSTRACT

Methods and apparatus for determining at least one metabolic state of a subject using a nuclear magnetic resonance (NMR) monitoring device. The NMR monitoring device comprises at least one magnet configured to generate a primary magnetic field, a transceiver coil arranged within the primary magnetic field, wherein the transceiver coil is configured to apply a time series of radiofrequency (RF) pulses to a portion of a subject located within the primary magnetic field and detect an NMR signal generated in response to application of the time series of RF pulses, and an NMR spectrometer communicatively coupled to the transceiver coil. The NMR spectrometer is configured to process the detected NMR signal to determine at least one metabolic state of the subject.

26 Claims, 14 Drawing Sheets

(51) Int. Cl.

| | | |
|---|---|---|
| *G01R 33/34* | (2006.01) | |
| *G01R 33/28* | (2006.01) | |
| *G01R 33/44* | (2006.01) | |
| *G01R 33/383* | (2006.01) | |
| *G01R 33/30* | (2006.01) | |
| *G01R 33/38* | (2006.01) | |
| *G01R 33/465* | (2006.01) | |
| *G01R 33/36* | (2006.01) | |
| *G01R 33/422* | (2006.01) | |
| *G01R 33/389* | (2006.01) | |
| *G01R 33/3875* | (2006.01) | |

(52) U.S. Cl.
CPC ..... *G01R 33/288* (2013.01); *G01R 33/34092* (2013.01); *G01R 33/3621* (2013.01); *G01R 33/3628* (2013.01); *G01R 33/3804* (2013.01); *G01R 33/422* (2013.01); *G01R 33/448* (2013.01); *G01R 33/465* (2013.01); *A61B 5/6824* (2013.01); *A61B 5/6825* (2013.01); *A61B 5/6829* (2013.01); *A61B 2503/10* (2013.01); *A61B 2560/0431* (2013.01); *G01R 33/302* (2013.01); *G01R 33/34053* (2013.01); *G01R 33/3678* (2013.01); *G01R 33/383* (2013.01); *G01R 33/3808* (2013.01); *G01R 33/389* (2013.01); *G01R 33/3875* (2013.01)

(58) Field of Classification Search
CPC ... A61B 5/6825; A61B 5/6826; A61B 5/6829; G01R 33/288; G01R 33/302; G01R 33/34053; G01R 33/34092; G01R 33/3621; G01R 33/3628; G01R 33/3678; G01R 33/3804; G01R 33/3808; G01R 33/383; G01R 33/3875; G01R 33/389; G01R 33/422; G01R 33/448; G01R 33/465

See application file for complete search history.

(56) References Cited

U.S. PATENT DOCUMENTS

| | | | | |
|---|---|---|---|---|
| 2008/0042650 | A1* | 2/2008 | McDowell | G01R 33/34 324/318 |
| 2008/0111548 | A1* | 5/2008 | Yamamoto | G01R 33/34053 324/322 |
| 2008/0111550 | A1* | 5/2008 | Freytag | G01R 33/3628 324/322 |
| 2008/0319293 | A1* | 12/2008 | Looney | A61B 5/05 600/365 |
| 2010/0239142 | A1* | 9/2010 | Dannels | G01R 33/246 382/131 |
| 2010/0256481 | A1* | 10/2010 | Mareci | G01R 33/341 600/423 |
| 2014/0111202 | A1* | 4/2014 | Wald | G01R 33/383 324/309 |
| 2015/0018638 | A1* | 1/2015 | Shames | G01R 33/448 600/301 |
| 2015/0168322 | A1* | 6/2015 | Alocilja | G01N 24/08 435/7.1 |
| 2016/0011290 | A1* | 1/2016 | Iannello | A61B 5/055 600/309 |

OTHER PUBLICATIONS

Melo et al., FPGA-based Digital Direct-Conversion Transceiver for Nuclear Magnetic Resonance Systems, 2012 (Year: 2012).*
Translation of CN102435967B—Temperature servo system applied to nuclear magnetic resonance magnetic circuit and resonance frequency searching method—Google Patents.*

* cited by examiner

US 11,439,313 B2

SMALL FORM FACTOR DIGITALLY TUNABLE NMR IN VIVO BIOMETRIC MONITOR FOR METABOLIC STATE OF A SAMPLE

CROSS-REFERENCE TO RELATED APPLICATIONS

This application claims the benefit of U.S. Provisional Patent Application Ser. No. 62/336,887, filed May 16, 2016, entitled "Hydration Monitoring Magnetic Resonance Wearable," the entire contents of each of which is incorporated by reference herein.

BACKGROUND

Metabolomic nuclear magnetic resonance (NMR) spectroscopy studies an organism's chemical phenotype in response to environmental factors such as diet, aging, and disease. NMR data is highly reproducible, quantitative over a wide dynamic range, and able to determine unknown compound structures. Additionally, NMR is non-destructive and chemically specific—allowing for metabolic pathway tracking in a living organism in vivo. In vitro NMR methods have routinely matriculated into the in vivo clinical realm, however, metabolic monitoring on a continuous basis (e.g., every few minutes or hours) for humans has so far been elusive as expensive and bulky hardware confines high-field NMR systems to the well-funded research laboratory where only short term monitoring can be performed.

SUMMARY

Some embodiments are directed to a nuclear magnetic resonance (NMR) monitoring device. The NMR monitoring device comprises at least one magnet configured to generate a primary magnetic field, a transceiver coil arranged within the primary magnetic field, wherein the transceiver coil is configured to apply a time series of radiofrequency (RF) pulses to a portion of a subject located within the primary magnetic field and detect an NMR signal generated in response to application of the time series of radiofrequency (RF) pulses, a tuning circuit coupled to the transceiver coil, wherein the tuning circuit is configured to adjust, during operation of the NMR monitoring device, a resonant frequency of the transceiver coil to a frequency associated with the primary magnetic field, and an NMR spectrometer communicatively coupled to the transceiver coil. The NMR spectrometer is configured to adjust, during operation of the NMR monitoring device, a frequency of the RF pulses in the time series of RF pulses based on the frequency associated with the primary magnetic field, and process the detected NMR signal to determine at least one metabolic state of the subject.

Other embodiments are directed to a nuclear magnetic resonance (NMR) monitoring device. The NMR monitoring device comprises at least one magnet configured to generate a primary magnetic field, a transceiver coil arranged within the primary magnetic field, wherein the transceiver coil is configured to apply a time series of radiofrequency (RF) pulses to a portion of a subject located within the primary magnetic field and to detect an NMR signal generated in response to application of the time series of radiofrequency (RF) pulses, and an NMR spectrometer having a software defined radio (SDR) architecture, wherein the NMR spectrometer is communicatively coupled to the transceiver coil. The NMR spectrometer comprises digital pulse generation circuitry configured to generate a digital representation of the time series of RF pulses, a digital-to-analog converter configured to convert the digital representation of the time series of RF pulses to an analog signal provided to the transceiver coil, an analog-to-digital converter configured to convert the detected NMR signal to a digital signal, and digital receive circuitry configured to process the digital signal to determine at least one metabolic state of the subject.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Figure 1:
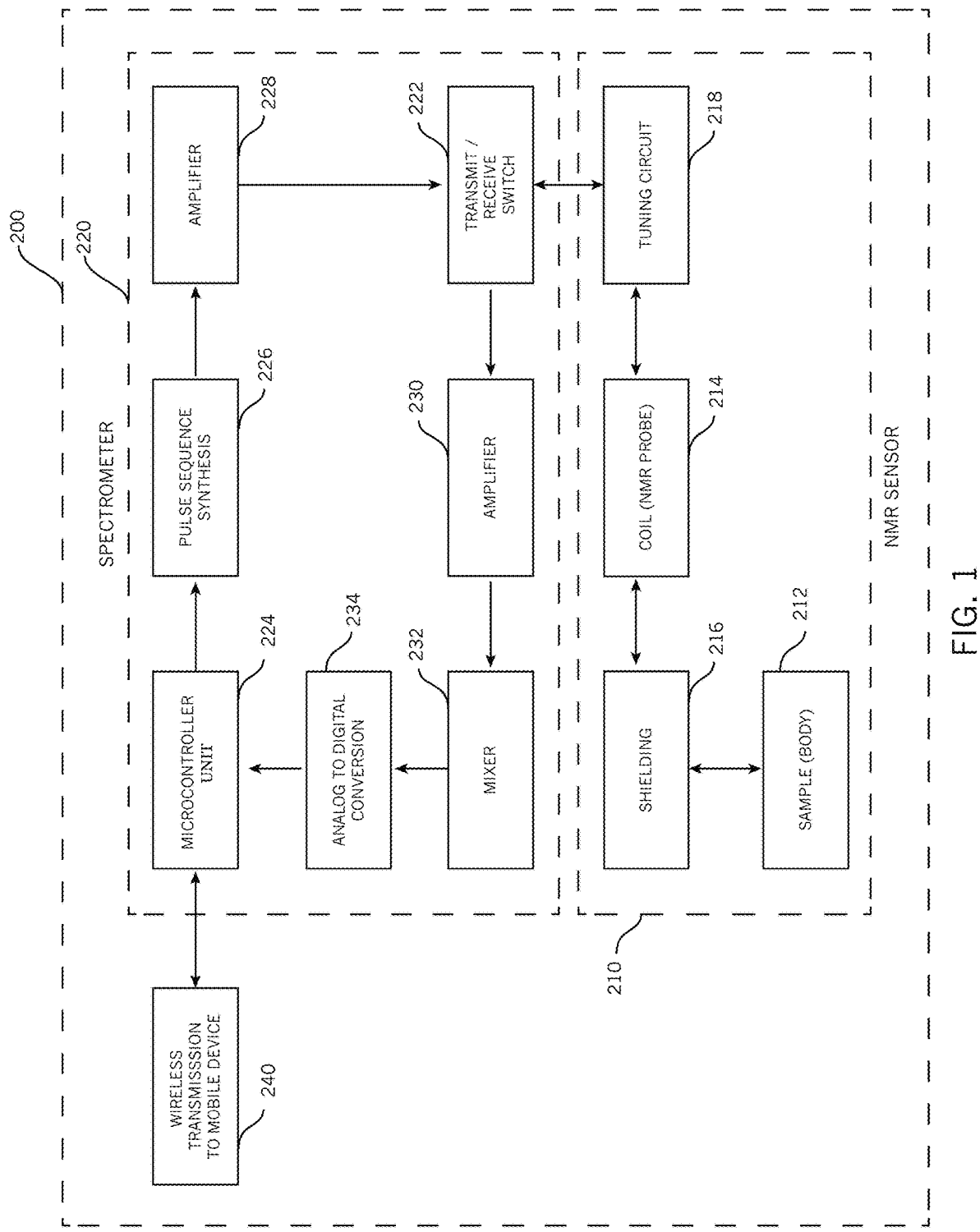
FIG. 1 illustrates a block diagram of an NMR monitoring device in accordance with some embodiments.

Advancements in the field of miniaturized NMR, over the last decades, have opened up the possibility of a low-cost and compact commercially-available NMR system. However, to date, no such product has been developed. Commercial efforts have predominately focused on building bench top laboratory systems; in essence, replacing only the super conducting magnet of a conventional high-field NMR system with a permanent magnet, while leaving in place all other hardware commonly used in high-field NMR systems. Existing miniaturized NMR systems are, thus, not typically specialized to a particular application and retain many of costly and bulky hardware elements of larger commercial systems.

The lack of a commercially available portable NMR system may be attributed, at least in part, to the fact that the sensitivity of NMR is directly correlated with the magnetic field strength at which it operates; that is, high-field NMR systems are able to measure a wider range of analytes precisely. Research in the fields of hyperpolarization and functionalized nanoparticles, among others, offer the promise of circumventing this problem by amplifying otherwise difficult to measure signals. However, many of these methods are invasive, expensive, and limited in scope.

While portable low-field systems are inherently less sensitive, their flexible architecture facilitates non-laboratory tethered prolonged analyte tracking; which is useful for in vivo applications. For example, time resolved in vivo data collected from a subject can be used to track global trends associated with changes in health status. In such an application where a single high abundance analyte is tracked in time, low-field sensitivity deficiencies are less important so long as the system can be made portable. Some embodiments are directed to a portable NMR spectrometer tailored to a specific application (e.g., hydration monitoring) capable of measuring NMR signals at low magnetic field strength (e.g., 0.025-1.4 Tesla).

Some embodiments are directed to techniques for addressing challenges for designing a portable NMR spectrometer including, but not limited to, designing compact and inexpensive magnetic-field stabilization via thermoelectric elements, active transceiver coil retuning, reducing the cost and footprint of the spectrometer, and reducing the size of the fully assembled device for portability.

NMR experiments that require signal averaging necessitate implementation of techniques for ensuring stabilization of the primary magnetic field ($B_0$). Permanent magnets are particularly susceptible to field drift as small temperature changes cause large fluctuations in magnetic field strength and the corresponding Larmor frequency ($\omega_0$). Conventional NMR systems often implement variable air temperature control systems that are composed of expensive and bulky instrumentation. Some embodiments are directed to an alternative field control method that does not require such instrumentation.

The inventors have recognized and appreciated that an in vivo NMR monitor developed in accordance with some embodiments need not be highly sensitive if, for example, post-processing routines can be applied to collected data to elucidate global trends. One metabolite abundant enough to measure with a low-cost NMR system is water. Accordingly, some embodiments are directed to a NMR-based system for measuring hydration status.

Clinically, it is common practice to use multiple metrics in combination to assess hydration state, such as change in body mass, osmolality of urine or blood plasma, urine specific gravity, urine color, and bio-impedance measurement of total body water. For reasons of impracticality, high variability, and poor reliability, none of these tools are unilaterally used to determine hydration state.

Hydration state detection using miniaturized NMR spectroscopy offers the possibility of accurate and long term monitoring, linking a subject's actions with changes in hydration state. Continuous or frequent sampling of hydration state biometric information may provide sufficient data density to resolve global trends associated with a subject's overall health. In effect, rate-of-change hydration state tracking may provide insights into a monitored subject's metabolism. Some embodiments described herein relate to a portable NMR system configured to measure a subject's hydration state. However, it should be appreciated that other embodiments more generally apply to using NMR techniques to assess a subject's metabolic state, with water being an example of one such metabolite.

Some embodiments are directed to a fully automated, inexpensive miniaturized NMR spectrometer designed to non-invasively track a subject's hydration state and metabolism in vivo. In some implementations, the device performs a Car-Purcell-Meiboom-Gill (CPMG) experiment, in which an aggregated relaxation rate is measured from an acquired $^1$H free induction decay (FID) signal. The relaxation rate is dependent on both the subject's tissue composition (e.g., intracellular, interstitial, extracellular, or vascular) and hydration state (e.g., water volume). As used herein, relaxation rate refers to one or more of longitudinal relaxation ($T_1$), transverse relaxation ($T_2$), inhomogeneous transverse relaxation $T_2^*$, or longitudinal relaxation in the rotating frame ($T_{1\rho}$). From the device sensitivity perspective, the contribution to aggregate relaxation from tissue composition remains constant over time (barring influences from degenerative diseases). By comparison, the contribution water makes to aggregate relaxation fluctuates on a much shorter time scale. In essence, the aggregate relaxation time represents the tissue-weighted relaxation time of water. Thus, the aggregate relaxation time changes with the abundance of water in the measured tissue. An NMR spectrometer designed in accordance with some embodiments is configured to measure a relaxation rate measurement on a localized part of the subject's body using a technique known as NMR relaxometry. This localized measurement acts as a proxy for detecting changes in overall body hydration. Body hydration, regardless of location, changes at relatively the same rate for a subject in homeostasis. Unequal distribution of water can occur in the body if the subject is exposed to either environmental pressures or dynamic stress (e.g., exercise).

An NMR spectrometer designed in accordance with some embodiments is configured to measure a relaxation rate measurement on a localized part of the subject's body using a technique known as NMR relaxometry. This localized measurement acts as a proxy for detecting changes in overall body hydration. Body hydration, regardless of location, changes at relatively the same rate for a subject in homeostasis. Unequal distribution of water can occur in the body if the subject is subjected to either environmental pressures or dynamic stress (e.g., exercise).

Some embodiments are directed to using hydration state data combined with processing routines, to monitor for changes in a subject's metabolism. For example, the rate-of-change in a subject's hydration profile may be related to the efficiency at which the metabolism is working—called metabolic rate. This technique is expected to be particularly effective in cases when the subject is at homeostasis and less effective when the subject is under varying environmental influences or performing physical exercise, as modeling the varying experimental factors in such as stressed condition may be difficult, as discussed in more detail below.

FIG. 1 illustrates an NMR spectroscopy device configured to perform a NMR relaxometry experiment in accordance with some embodiments. In one implementation, the device may be configured to assess a subject's hydration state periodically (e.g., at least once per day with repeated measurements anticipated at regular daily or hourly intervals) or on-demand. Some embodiments include a display indicator integrated with the device to display a result of the relaxometry experiment. In other embodiments, information related to a result of the relaxometry experiment may be sent to a network-connected device (e.g., a smartphone) via a wireless and/or wired connection for display. The network-connected device (e.g., a desktop or mobile computer) may be configured to accept and host incoming data from the NMR spectrometer device using a software application installed locally on the network-connected device.

In some embodiments, at least some of the hosted data on the network-connected device may be transferred to one or more network-connected computers (e.g., a server), where the data may undergo processing including, but not limited to, deconvolution, apodization, normalization, regression, and Fourier transform. In some embodiments, trend prediction routines are used to identify rates-of-change in the processed data. At least some of the processed data may be returned to the software application executing on the network-connected device which may present one or more metrics, graphs, or other visualizations based on the processed data. In some embodiments, the visualizations may include a risk score that rates the subject's hydration state (e.g., on a scale from 1-10). In other embodiments, the visualizations may include a risk score matrix which assigns risk based on subject's hydration state and one or more other subject specific parameters, including but not limited to heart rate, blood pressure, temperature, and surveyed symptom status.

An NMR monitoring device designed in accordance with some embodiments may be used to monitor a hydration state of a patient diagnosed with or at risk for congestive heart failure (CHF). For this application, the risk score may relate to the subject's accumulation of water in the body and their likelihood of developing congestion. An alternative application of some embodiments may be monitoring dehydration in athletes. In this application, the risk score may relate to the likelihood of becoming dangerously dehydrated. In the former case of CHF monitoring, the software application may also facilitate patient-doctor interactions via a built-in messaging service. The physician may have direct access to the patient's data and be able to provide guidance on treatment and management.

FIG. 1 illustrates a functional block diagram of components of a NMR monitoring device 200 in accordance with some embodiments. Monitoring device 200 includes a sensor 210 configured to generate and tune a magnetic field and a spectrometer 220 configured to measure metabolic information from a sample 212 (e.g., a portion of a subject's body) when placed in the magnetic field. Sensor 210 includes one or more transmit/receive coils 214 configured to operate as an NMR probe by providing a secondary magnetic field $B_1$ in the presence of a primary magnetic field $B_0$ generated by an array of magnets (not shown). In some embodiments, the primary $B_1$ induction coil is designed as both a transmitter and receiver (i.e., a transceiver coil) and can be made of, at least in part, materials including, but not limited to, copper, gold, silver, aluminum, palladium, or a combination thereof. In some embodiments, a solenoid coil geometry is selected based on its ability to produce the highest possible efficiency related to $B_1$ amplitude for a given current passing through the coil wires, though in other embodiments a different coil geometry may be used. The sensitivity of an arbitrary coil geometry can be defined as:

$$S = \frac{B_1}{(I_0 \sqrt{R})} = \sqrt{\eta Q}$$

where $I_0$ is the current amplitude, R is the resonant coil resistance, $\eta$ is the filling factor of the resonant coil and Q is its quality factor. $B_1$ can be defined as:

$$B_1 = \frac{3}{10,000} \sqrt{\frac{PQ}{Vf}}$$

where P is transmitter power in watts, V is the coil volume in cubic centimeters, and f is the resonance frequency in megahertz.

Sensor 210 also includes shielding component 216 configured to shield coil(s) 214 from external sources of noise to improve the sensitivity of the NMR measurements. In some embodiments, several insulating layers of electromagnetic shielding may be incorporated in to the design of the device. For example, a first layer of copper and aluminum shielding may be present at the exterior walls of the primary enclosure (e.g., a Faraday cage). Additionally, each printed circuit board may be enclosed in a shielded enclosure to prevent crosstalk interference between spectrometer modules. Additionally, the primary magnet holder may be wrapped in copper tape to guard against induced eddy currents from the printed circuit boards. An additional layer of copper tape may also be placed between the $B_0$ magnet array and the $B_1$ inductor coil to mitigate and magnetoacoustic ringing. While multiple layers and different types of shielding are described, it should be appreciated that not all embodiments require the use of all described types of shielding, as some embodiments may include fewer or more shielding techniques depending on the particular application of the device.

Sensor 210 further includes tuning circuit 218 configured to tune the resonant frequency of coil(s) 214 to match the operating frequency of the coil(s) to the frequency of the primary magnetic field $B_0$ as it drifts over time. The transceiver coil 214 is connected to the tuning circuit 218, which, in combination with the inductor coil, resonate at the Larmor frequency of the primary magnetic field. Tuning circuits for use in some embodiments may vary in design depending on the desired properties of the transceiver coil and the application. A capacitive top-coupling RLC circuit may be used in the tuning circuit of some embodiments of the NMR monitoring device. 50 Ohm impedance matching may be achieved by adjusting a variable capacitor located in series with the induction coil. Other implementations of the probe RLC tuning circuit may implement, but are not limited to a capacitive voltage division circuit, an inductive voltage division circuit, and a mutual inductance coupling circuit. Other embodiments of the transceiver induction coil circuit may implement a double tuned RLC circuit corresponding to multiple nuclei (e.g., $^1H$, $^{13}C$, $^{15}N$ and $^{31}P$).

Spectrometer 220 includes a transmit/receive switch 222 configured to interact with the tuning circuit 218 and/or the primary transmit/receive coil 214 in the sensor 210 to create a secondary magnetic field B1 used to interrogate a metabolic property of the sample 212. In one implementation transmit/receive switch 222 may be implemented using a PIN diode. Alternatively, transmit/receive switch 222 may be replaced with digital circuitry in a low-power design, an example of which is discussed in more detail below.

Spectrometer 220 also includes a microcontroller unit 224 and a pulse sequence synthesis component 226, which may include a direct digital synthesizer (DDS) signal generator. Spectrometer 220 may further include an amplifier component 228 which may include a preamplifier and transmit power amplifier (TPA). In one implementation, the TPA may include eGaN field effect transistors (FETs) in a current mode class-D (CMCD) topology, a buck modulator for amplitude and eGaN FETs for power control. In some embodiments, a CMCD topology-based TPA is selected for its high efficiency switching properties at frequencies between 1-60 MHz. eGaN FETs are desirable as they reduce spectrometer power consumption significantly. A downside of using a CMCD is that amplitude modulation is not possible directly from the RF signal that is being amplified. Therefore, a buck modulator may be used to change the voltage at which the amplifier operates. In some embodiments, the buck modulator may be used only to change the power. However, in other embodiments, the buck modulator allows for fast changes and may also be used for amplitude modulation.

The incoming signal from the transmit/receive coil 214 to the receive system is generally weak, on the order of microvolts, therefore the received NMR signal is amplified through a multi-stage system of low noise amplification circuitry. Accordingly, spectrometer 220 also includes low-noise receive amplifier 230 in addition to other components such as bandpass filters and an RF splitter (not shown) for processing a received NMR signal. Some embodiments implement a heterodyne receive chain architecture where the amplified signal is split and mixed down to baseband with two independent channels: an in-phase local oscillator and a 90° phase offset local oscillator using downmixing circuitry 232. Downmixing reduces the sampling requirements of the analog to digital conversion system from the megahertz range to the kilohertz range, and the two-channel system allows for quadrature detection of the full FID signal. Note that the heterodyne receive chain requires maintaining a frequency offset ($|f_0-fl|$) (e.g., 1 kHz) during the downmixing stage to ensure that robust and reliable measurements are obtained. Spectrometer 220 also includes an analog-to-digital converter (ADC) 234 configured to convert the analog downmixed signal to a digital signal for processing by microcontroller unit 224. In one implementation, printed circuit boards (PCBs) are fabricated on one side using a surface mount reflow oven and on the reverse side with manual soldering.

Spectrometer 220 may also include a communications interface 240 configured to transmit information from microcontroller unit 224 to a local or network-based external device such as a smartphone or network-based server. At least some of the data processing performed by a network-based server may be implemented locally on the NMR monitoring device 200. For example, some embodiments include hardware configured to perform a Fast Fourier Transform (FFT) of the time-domain data prior to digitization. In situations where network connectivity is not available or possible, local FFT processing may be implemented. Implementations for including a local FFT hardware include, but are not limited to, adding additional CPU processing power to microcontroller unit 224 or inclusion of an FFT application specific integrated circuit (ASIC).

Several of the components of the NMR monitoring device 200 are described in more detail below.

Example Magnet Geometries

Figure 2:
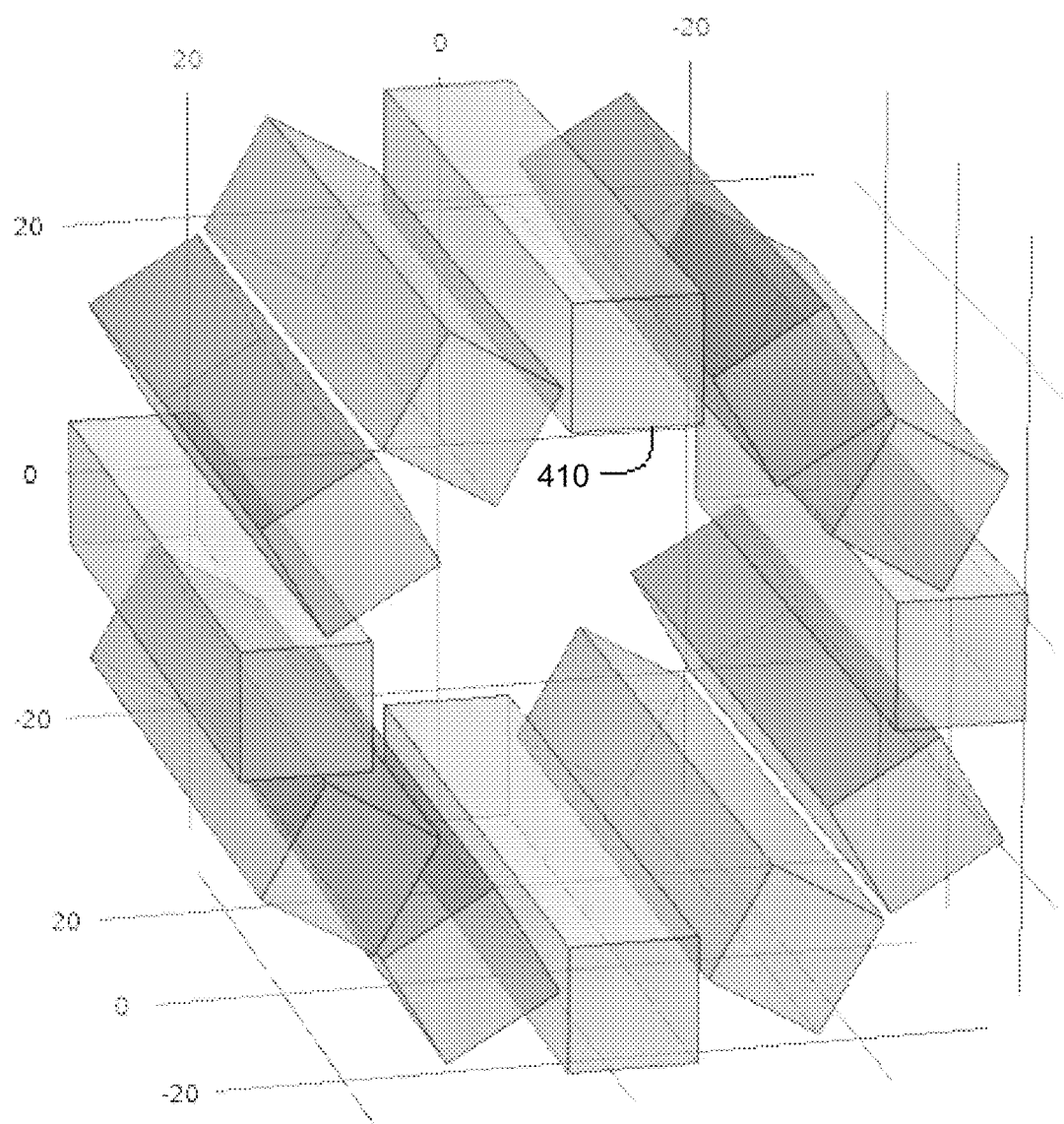
FIG. 2 schematically illustrates an array of magnets arranged in a Halbach configuration.

The coil design geometry for generating the $B_0$ field is dependent, at least in part, on the portion of the sample (i.e., subject) intended to be interrogated using the device. FIG. 2 shows an example of a Halbach array of neodymium magnets 410 (permanent magnets) may be may be used in accordance with some embodiments to generate a $B_0$ field. In one implementation, magnets 410 may be implemented as N52 grade NdFeB magnets with a Ni—Cu—Ni coating. In another implementation, magnets 410 are implemented as SmCoFeCuZr or SmCo alloy magnets. Magnets 410 may be arranged using a holder constructed of a polymer (e.g., acetal copolymer, SU-8 epoxy, ABS, Polycarbonate, or PEEK) or, optionally, a NMR silent material (e.g., PMMA, polyurethane, borofloat glass, PTFE, PCTFE/Kel-F Neoflon, or another fluoropolymer). The magnet geometry may be simulated, using an electromagnetic finite element modeling package (e.g., COMSOL or HFSS), prior to construction. The geometry dimensions used in the simulation can be determined based on factors including, but not limited to, a desired minimum inner diameter and a desired magnetic field strength corresponding to the upper bound output frequency of the amplifier.

Coil Tuning

The inventors have recognized and appreciated that one of the challenges with implementing a NMR monitoring device involves fluctuations in the $B_0$ field that can occur due to the strong dependence of the magnetic field on temperature—called field drifting. Some conventional high-field systems compensate for field drifting using a variable temperature control system, which typically are expensive and not portable. Some embodiments include a variable air temperature control system to mitigate fluctuations in the $B_0$ field. Alternatively, some embodiments include thermoelectric Peltier elements configured to supply temperature control over the $B_0$ magnet. These thermoelectric elements can either heat or cool the magnets, depending on the direction of the applied electric current, in order to attempt to maintain a constant magnet temperature, and therefore $B_0$ field strength, even in fluctuating environmental conditions. In some embodiments, metallic heat sinks may be used increase heat flux and/or increase the efficiency of the system. In either of these implementations, the heating/cooling elements are controlled by a feedback loop system sensing the temperature of the magnet.

Loss of device sensitivity occurs when the Larmor frequency of the $B_0$ field drifts significantly away from the resonant frequency of the induction coil. Field drift is problematic when performing averaging experiments, but can also be an issue in single scan quantitative experiments that are spaced apart in time, allowing for environmental conditions to change, and thus introduce potential error across multiple measurements. In some embodiments, rather than maintaining the magnetic field strength, the resonant frequency of the primary transmit/receive coil circuit is automatically adjusted to match the Larmor frequency associated with the drifting $B_0$ field. Some embodiments include a digitally-controlled system which detects changes in either the temperature or magnetic field and, in response, changes the capacitance values of the tuning circuit 218. Implementation of this concept can include a feed-forward automatic controller system.

Figure 3:
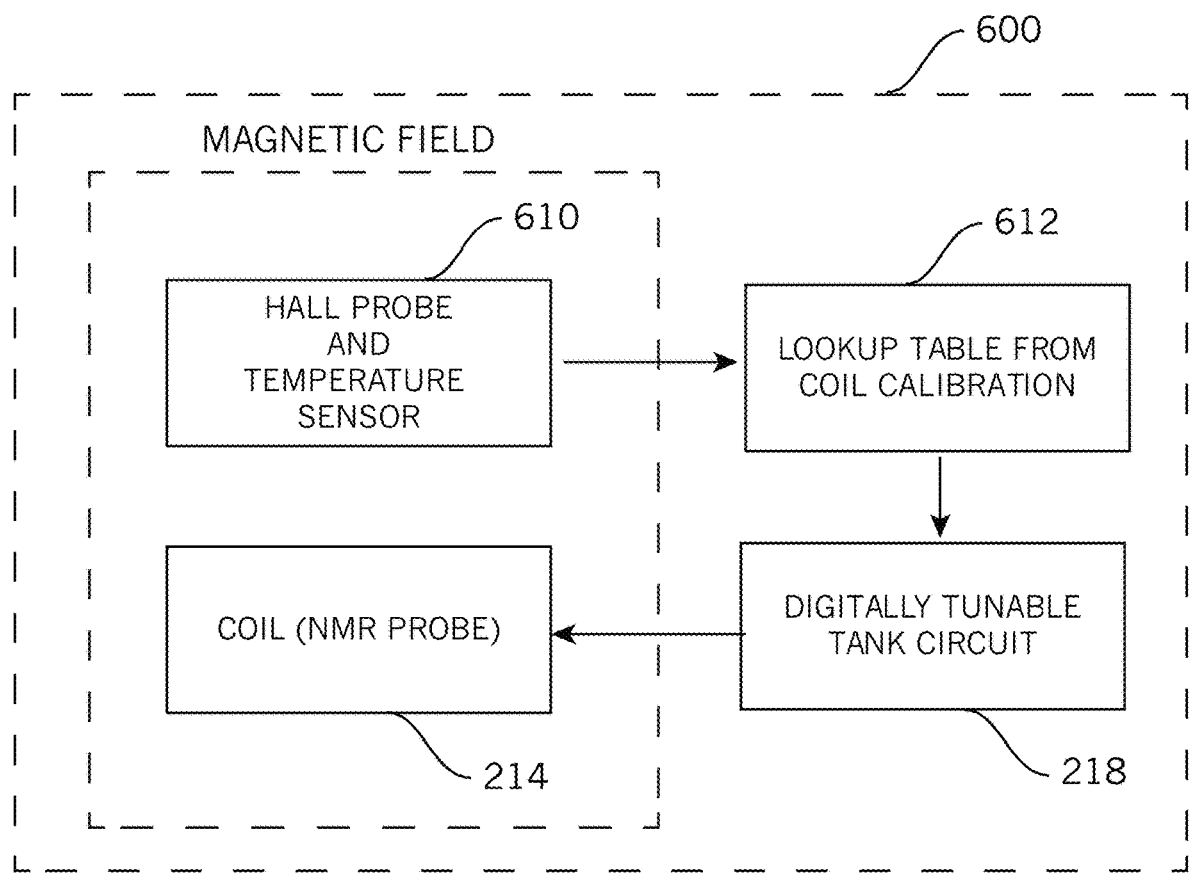
FIG. 3 illustrates a block diagram of a tuning circuit that may be used in accordance with some embodiments.

FIG. 3 illustrates a block diagram of a transmit/receive coil tuning circuit that may be used as a feed forward controller in accordance with some embodiments. As shown, one or more properties of the magnetic field environment within which coil(s) 214 are used are measured by field sensors 610 such as a temperature sensor (e.g., a thermometer) and/or a magnetometer (e.g., implemented as a Hall-effect probe) configured to detect changes in the $B_0$ field. The feed-forward controller makes adjustments based on measurements from the field sensors 610, using pre-calibrated data 612. For example, the pre-calibrated data 612 may specify a relationship between the S-parameters (e.g., $S_{11}$ or $S_{12}$) of the NMR probe 214 and a particular temperature or $B_0$ value. In some embodiments, tuning circuit 218 includes digitally tunable capacitors directly connected to the output of the feed-forward controller as shown. Thus, a change in magnetic field detected by field sensors 610 can be matched with a change in coil frequency, making the output of the overall system robust against environmental variations. Additionally, this approach allows for signal averaging over an extended period of time when the magnetic field is expected to drift significantly due to changes in room temperature. While some embodiments of the NMR monitoring device may be sensitive enough to record a signal from a single experiment, averaging acquired signals over time may help clarify convoluted data.

In embodiments that include a Hall-effect probe or other magnetometer-type sensor, data recorded by the probe may be passed to the microcontroller unit 224, which converts the field strength into a Larmor frequency of the nuclear species of interest, for example, $^1$H hydrogen, via the gyromagnetic ratio of the nuclide. The microcontroller unit 224 may then use this input to control two outputs: the frequency of the excitation pulse sequence and the tuning of the transceiver coil circuit by tuning circuit 218.

The tuning and matching capacitors of the transceiver coil circuit may include digitally tunable capacitors, which function as the control variable (i.e., output). The microcontroller unit may be configured to adjust the digital capacitor values in response to field changes to match a stored pre-calibration data set. The pre-calibration routine may include steps of attaching the transceiver induction coil circuit to a vector network analyzer (VNA) and cataloging its response to changing digital capacitor values creating a one-to-one mapping of desired coil tuning to these values. The feed-forward controller does not measure the tuning response of the coil itself, as would be the case with a feedback-based controller, but instead users the stored pre-calibration data to determine how to tune the transceiver coil using tuning circuit 218.

In embodiments where the measured process variable is temperature, the pre-calibrated data may associate temperature with a particular $B_0$ field value. Yet another embodiment includes both temperature and $B_0$ field input as measured process values.

Some alternatives to a digitally-tuned capacitor in tuning circuit 218 include a varicap diode or a logic controlled capacitor array. The controller logic could also vary greatly from the above example involving a feed-forward controller. In some embodiments, adjustments to the digital capacitor values are only made during non-measurement times.

Another alternative implementation for tuning transmit/receive coil 214 in accordance with some embodiments includes performing a calibration sequence prior to a measurement, using a reference sample with a known output signal, such as a vial of water that can be supplied with the device. The calibration sequence may involve performing several measurements sequentially for a variety of coil tunings (with commensurate changes in excitation pulse frequency) and then selecting the values that correspond to the known reference signal. Alternatively, instead of performing a sweep of values, the output signal of the first test may be used to inform subsequent tests in a guess-and-check fashion, creating a form of feedback control to tune the system before an actual subject measurement is performed. An advantage of this technique is that it eliminates the need for additional sensors such as temperature sensor or Hall-effect probes.

Figure 4:
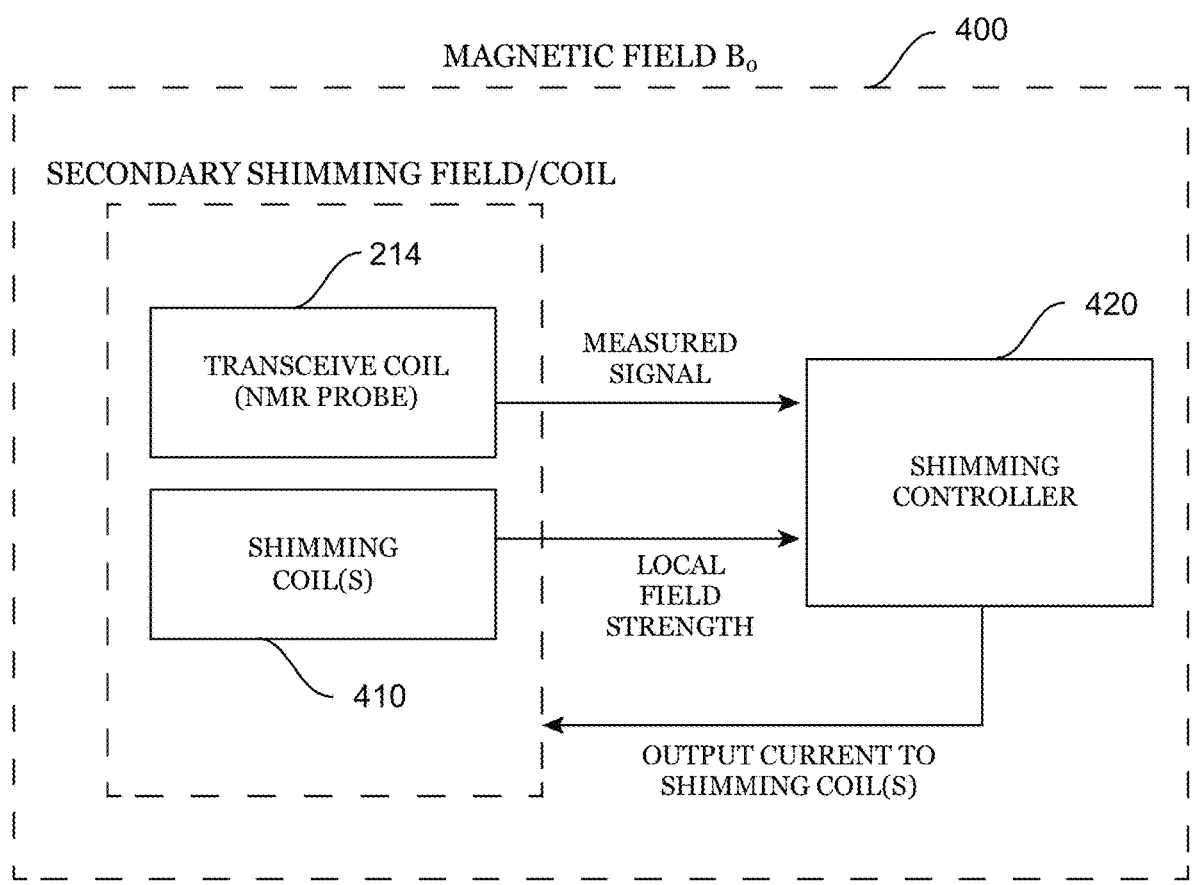
FIG. 4 illustrates a block diagram of a shimming system for use with some embodiments.

FIG. 4 shows a block diagram of a shimming system 400 that may be used in accordance with some embodiments. Shimming system 400 includes one or more magnetic field homogenizing shimming coils 410 and a feedback loop controller 420 configured to optimize shimming coil values for the shimming coil(s) 410. Inhomogeneities in the primary $B_0$ magnetic field can be compensated for with secondary magnetic fields produced by electromagnets arranged spherical harmonic geometries—called shims. Many commercial superconducting magnets have cryo-shims, room temperature shims, and/or ferromagnetic shims. While cryo-shims are onerous to adjust, and are typically set once by the factory, room temperature shims can be adjusted by the user manually or using a software-implemented auto shim routine. This software typically uses a numerical method driven optimization using the spectral line shape as a guide. Some embodiments of the NMR device described herein that includes shims may optimize the shim current values locally, where the input variable being optimized is the intensity of signal from a subject. Using a feedback loop control technique rather than a more robust numerical routine is possible because the sample (e.g., a subject's finger) is well understood and predicable, even across different subjects.

In another embodiment of a feedback loop shim controller, the feedback routine may use data from hall probes to optimize the signal instead of using the spectral line shape. In such an embodiment, the hall probes are symmetrically positioned in the device and the feedback loop maximizes each readout value while maintaining equal intensity readings across each. The assumption being that distortions in the primary field, created by the introduction of the sample, will also create distortions in the region where the hall probes is located. Thus, by optimizing the intensity readout value from the hall probes, the field inhomogeneities are compensated.

Noise Reduction

Another technical challenge that the inventors have identified in designing an NMR metabolic monitor involves the influence of external electric fields (E-fields), which cause a significant increase in the ambient background noise detected by the receive coil when the device is not used in a shielded enclosure (e.g. a Faraday cage). Some embodiments are configured for use in an environment that does not include shielded enclosure. While the measurement is localized, a subject's body acts as an antenna for ambient electric fields. The resulting noise floor is of greater magnitude than the experiment signal. It is therefore important for the receive coil to be electrically decoupled from the subject to suppress effects from E-fields. Some embodiments are directed to techniques for electrically decoupling the subject from the receive coil. Any of the below described techniques may be used alone or in combination to reduce the effect of external noise on making NMR measurements in accordance with some embodiments.

Figure 5:
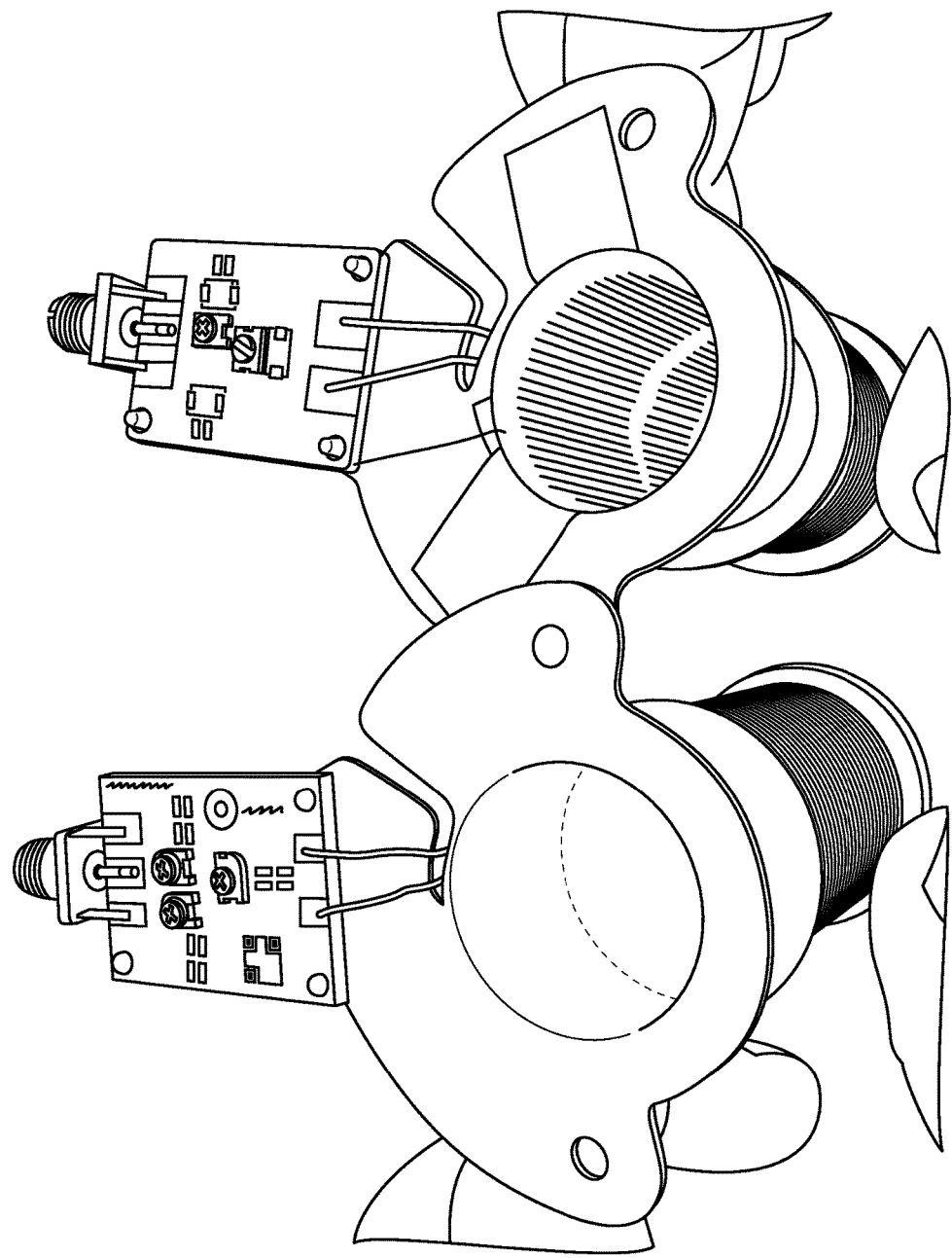
FIG. 5 illustrates conceptual images of an NMR monitoring device in accordance with some embodiments.

In one such technique, a grounded metal grating is inserted between the sample (e.g., a subject's finger) and the receive coil to provide electrical decoupling between the receive coil and E-fields generated by the sample. Some embodiments include a mesh grating (e.g., made of copper or another conducting material) arranged between the sample and the receive coil. The thickness, spacing and design parameters of the grating/mesh can be varied based on the geometry of the coil arrangement of the NMR device. FIG. 5 shows an example of a coil geometry for a finger-based device without (left) and with (right) a grating/mesh arranged between the receive coil and the sample to provide electrical decoupling. A conductive plate arranged between the sample and the receive coil would provide sufficient decoupling, though it would also eliminate the sample signal. Such an implementation also suppresses external E-fields, though these are generally of lower magnitude, and thus less concerning, compared to E-fields introduced locally by the subject. The presence of the grating has the downside of reducing the transceiver coil $B_1$ efficiency and penetration depth. However, the loss of sensitivity is balanced by the gain in noise immunity. The SNR of the measurement is therefore significantly increased as a result of implementing the grating/mesh.

In some embodiments, the design, track spacing, thickness, and separation from the sample of the mesh grating may be optimized to reduce E-field noise contribution, which results from sample-coil coupling, and to increase the sample signal.

In another technique for electrically decoupling the receive coil from the sample, the sample may be grounded sufficiently resulting in a large reduction in the background noise level. For example, in embodiments in which a finger is the measured object, the remaining portion of the hand may be placed in contact with the ground plane at multiple points to ground the subject. Alternatively, the system may include a grounded wrist band that the subject wears during an NMR measurement.

As yet a further technique to reduce noise, some embodiments are directed to designing aspects of the transceiver induction coil to reduce the effects of external noise. In one such technique, a gradiometer-based coil design is used as an alternative to the solenoid coil design. Such a gradiometer-based coil design may be used to cancel ambient magnetic fields, thereby reducing external noise. Examples of gradiometer coils include a butterfly coil, also called a FIG. 8 coil and a split-loop resonator. In some embodiments, gradiometer-based coils are designed to be electrically balanced with no dipole moment.

Another noise reduction technique that may be used in accordance with some embodiments is to optimize the coil geometry for a particular application. The solenoid coil geometry described herein and shown in FIG. 2 is a coil design well suited for performing NMR measurements on a finger with a coil filling factor approaching 0.5. Optimizing the geometry in this arrangement may include, for example, determining the shape and spacing of coil turns based upon the thickness and girth of an average subject's finger. In some embodiments, coil dimensions are varied slightly along the sample as a way to generate a homogeneous $B_1$ field when loaded.

Alternatively, the $B_1$ transmit/receive coil in some embodiments may adopt one of several geometries with certain desirable properties. For instance, the saddle coil, the Alderman-Grant (AGR) coil, and the modified Alderman-Grant coil are geometries known to have good immunity to E-field noise. Some embodiments employ a non-cylindrical coil geometry.

Other techniques for reducing noise include, but are not limited to, using remote tuning for efficient sample-coil decoupling, using a PIN diode for active decoupling, using a balun in the tuning circuit 218 to mitigate sample-coil coupling, and reducing the receive chain analog circuitry to avoid signal deterioration.

Power Consumption

Another challenge that the inventors have identified in designing an NMR monitoring device with a small footprint is the power requirements of such a system. Spectrometer footprint size is partially tied to the power levels required. Rather than being general purpose NMR spectroscopy devices, some embodiments are tailored to performing one or only a small set of NMR-based measurements, which have relatively low power requirements. For example, performing $^1H$ relaxometry experiments on high abundance high gamma nuclei (e.g., water molecules) requires relatively low power as compared to other nuclei or cross polarization experiments. Accordingly, some embodiments are directed to an application-specific NMR spectrometer with reduced power requirements resulting in a more compact size than conventional systems.

The spectrometer schematically illustrated in FIG. 1 and described above includes primarily analog signal processing chain elements. However, the consequence of using an analog-based spectrometer is that analog signal processing circuitry requires a larger footprint area than equivalent digital integrated circuit alternatives. Additional or alternative power and/or size savings may be obtained by replacing one or more of the analog-implemented functions along one or both of the signal generation or receive chains with digital circuitry such as ASICs. Such ASICs are often designed for high-frequency, low-power communication applications and are, thus, inappropriate for many commercial research applications for which conventional high-field NMR spectrometers are designed.

An example of how at least some of the analog circuitry in the NMR spectrometer may be converted to digital circuitry is by using software defined radio (SDR) modeling, which is a field of research devoted to translating analog radio circuitry into digital circuitry. While the entire spectrometer architecture designed in accordance with some embodiments can be modeled after SDR systems, some components of the system, such as the transceiver circuit, must remain analog. Some embodiments address this problem by using a fast (i.e., up to 120 MSPS) digital-to-analog converter to transmit an excitation pulse to the induction coil and fast (i.e., up to 120 MSPS) analog-to-digital converter to receive the incident signal. This approach allows the entire spectrometer to be made digital while preserving the analog transceiver induction coil circuit.

Figure 6:
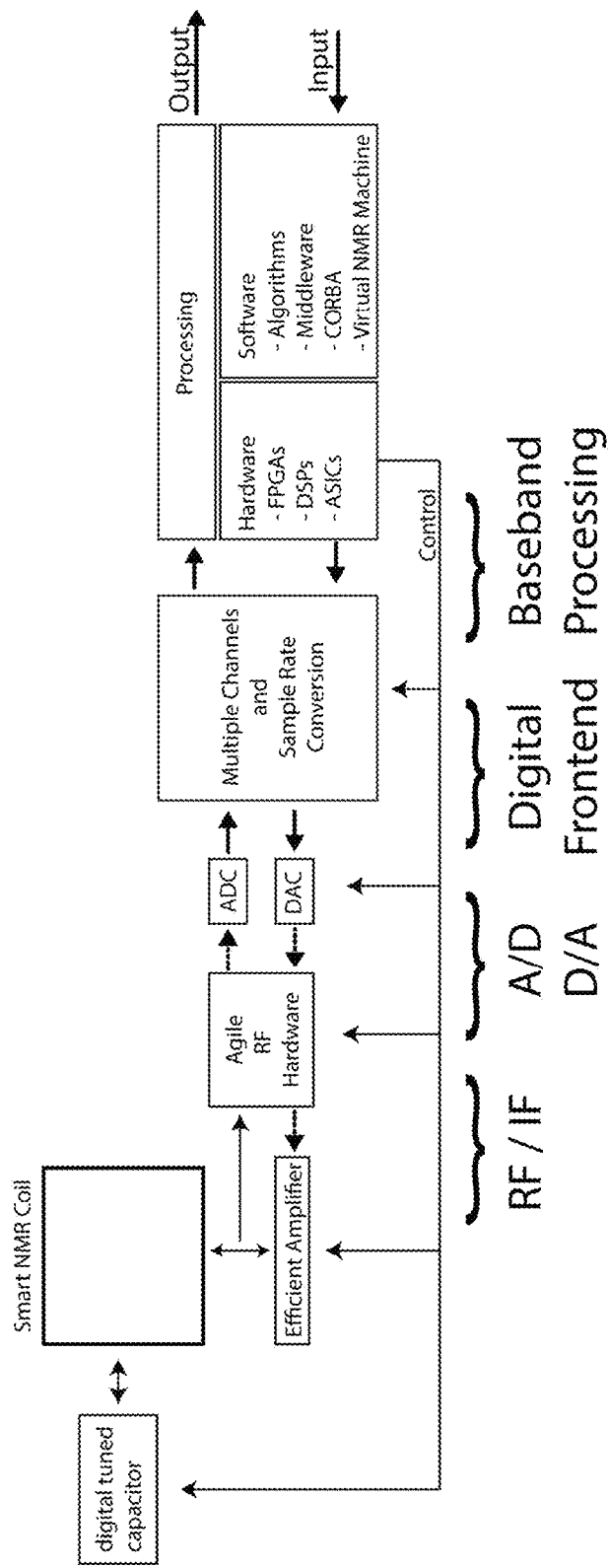
FIG. 6 illustrates a software defined radio (SDR) architecture implementation of an NMR monitoring device in accordance with some embodiments.

An SDR NMR architecture in accordance with some embodiments allows for a much greater flexibility and hardware simplification, as the digital domain allows for many different operations to be performed with the combination of software programming and digital signal processing. For instance, implementing effective steep bandpass filtering is difficult using analog components, but is comparatively easier in the digital domain. Still more capabilities can be added by integrating an optimizable field-programmable gate array (FPGA) integrated circuit (IC) into the SDR NMR device architecture. FIG. 6 illustrates a functional block diagram of a SDR NMR spectrometer designed in accordance with some embodiments.

Figure 7:
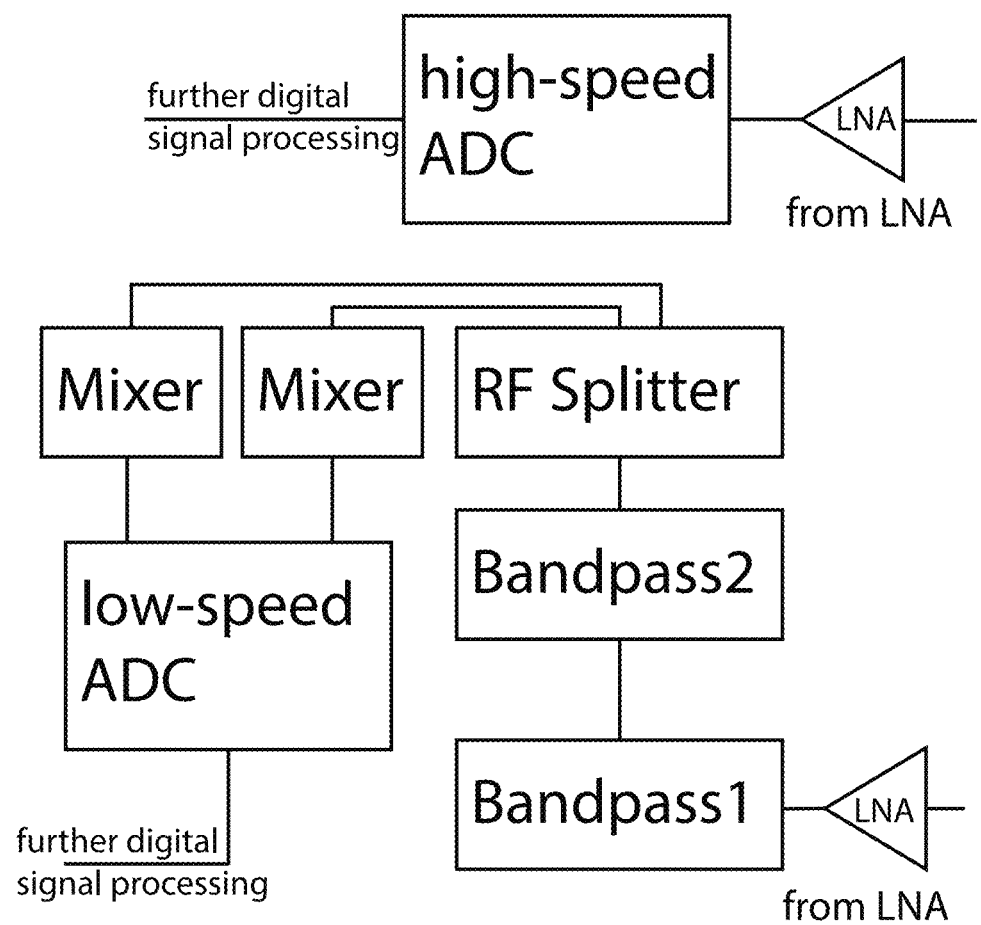
FIG. 7 illustrates a software defined radio (SDR) architecture implementation of an NMR spectrometer in accordance with some embodiments.

A specific example of how a SDR would be applied to NMR can be described specifically in the case of performing quadrature detection. In the analog spectrometer described above in connection with FIG. 1, the incident signal from the coil passes through a low noise amplifier, two bandpass filters, and a RF power splitter which splits the RF signal into two signals. These two RF signals are then downmixed with a local oscillator to baseband. A separate RF mixer is required for each channel. One of the local oscillators is phase shifted by 90°. Then both baseband signals are digitized with an ADC and combined to a digitally complex signal which is the FID signal. The above-described analog process requires a relatively large space envelope to implement. In some embodiments, some or all of the described components and accompanying circuitry (resistors, capacitors etc.) are replaced by a single high-speed ADC as shown in FIG. 7. This implementation leads to a significant reduction in PCB space and component count. All further operations, like the quadrature detection and bandpass filtering may be performed in the digital domain with no further degradation in signal quality.

Currently available commercial SDRs are generally not suitable for use in NMR. For example, such SDRs lack the transmit power that is necessary for performing NMR experiments (typically in the range of up to 10 W for short pulses for up to 10 us), and are usually optimized for certain frequency bands that are allowed for amateur radio. Such commercially available SDRs are also typically connected to a broadband antenna, whereas NMR uses an inductive coil tuned to a specific resonance frequency. NMR systems need a more flexible frequency range that is defined by the magnetic field strength. Some commercial SDR systems are also only for receive and lack the transmit channel completely.

Some embodiments are directed to replacing a smaller subset of the analog circuitry components of the NMR spectrometer with digital circuitry than that discussed above for an SDR-based design. Digital down conversion is a simplified alternative to the analog equivalent version. For example, replacing the analog down conversion circuitry is an intermediate step to a full SDR-based implementation that requires minimal architecture redesign. Accordingly, some embodiments eliminate the analog receive chain and RF frequency down mixing circuit and instead directly convert the received RF signal to digital at full frequency. By directly converting from analog to digital at the frequency of the NMR experiment, without first down converting to baseband, the receive chain can be significantly reduced in size. An additional benefit is that signal deterioration is avoided. In such an implementation, only a low noise amplifier is needed to provide the necessary first amplification stage, after which the signal is converted to digital and all further signal processing can be accomplished using software.

As discussed above, power consumption is a key limiting factor for many electronic systems, including a wearable or portable NMR device described herein. A constrained power supply severely limits the operation time of the system; as is the case with wearable devices, where smaller batteries are more comfortable for the user and hence more desirable. Some methods to reduce power consumption include:

Raising the threshold voltage to reduce subthreshold leakage.
  Power gating, using transistors, to selectively switch off circuitry when not in operation.
  Limiting the number of state changes.
  Lowering the overall voltage and relying on adiabatic circuits.

Some embodiments reduce the analog spectrometer footprint by replacing individual ICs with single chip solutions, such as an agile analog frontend, ideally all integrated into the microcontroller unit—that is, a microcontroller unit with an integrated DDS and ADC. This approach consolidates the respective IC packages in the microcontroller unit, significantly reducing component count and required board space. Further, specialized ICs offer better performance as compared to the equivalent analog component based circuit.

Figure 8:
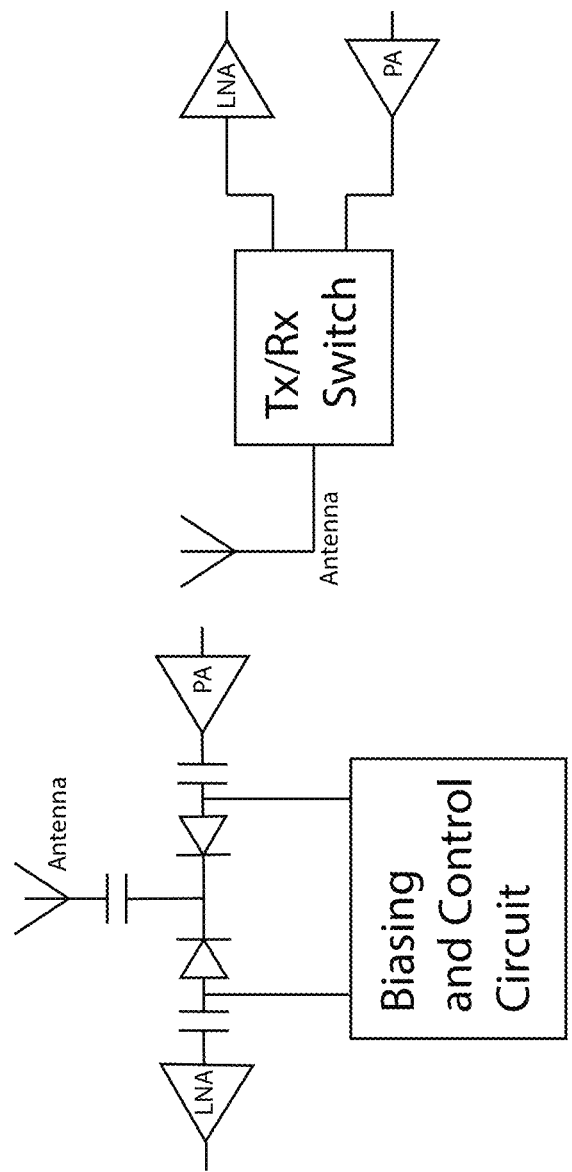
FIG. 8 illustrates a circuit diagram for a diode-based logic transmit/receive switch and an ASIC transmit/receive switch in accordance with some embodiments.

Other examples of analog circuitry can be implemented using digital circuitry in some embodiments include a transmit/receive switch ASIC, an example of which is shown in FIG. 8. As shown, the diode-based transmit/receive switch may be implemented using a CMOS single chip solution.

NMR Signal Quantification

As discussed above, an application of an in vivo NMR device designed in accordance with some embodiments is hydration monitoring. Some embodiments are directed to techniques for quantifying the NMR signal. The ERETIC (Electronic Reference To access In vivo Concentrations) or a related hardware-based technique for quantifying the NMR signal in accordance with some embodiments includes constructing a second spectrometer channel connected to a second transmitter coil. The second transmitter coil is placed in close proximity to the $B_1$ coil, such that when the $B_1$ coil is in receive mode the second transmitter coil detects the transmitted signal from the second coil. The second transmitter coil is calibrated such that a particular power level is correlated with a signal from a known amount of sample. Thus, the data recorded by the second transmitter coil include a signal from the subject and a pre-calibrated signal from the second channel. Using this technique, the NMR signal can be quantified when referenced to the artificial signal peak.

The hydration content for a subject is quantified in some embodiments using a reference calibration experiment. For example, a reference spectra from a calibration sample may be recorded prior to a subject measurement, and the result from the calibration sample may be compared to the recorded sample spectra. In some embodiments, a reference sample can be embedded into the device for use in recording a reference spectra. Another technique delivers a range of frequency calibration pulses and power levels mapped to stored calibration information.

Data Acquisition

In accordance with some embodiments, an FID generated by a simple 90°, or $\pi/2$, pulse experiment can be difficult to detect due to interference from long dead times and ring-down times. Therefore, an echo based experiment may be used to create time separation from such interference.

Once the raw data for a test is collected by the system in the form of 2-channel quadrature data of the time domain signal amplitude, the data is processed to further extract information. The data is segmented as a series of echoes elicited from the CPMG pulse train. Each segment of time series data is converted to the frequency domain via a complex Fourier transform of the quadrature data, to allow further signal processing. The amplitude of the signal peaks in the frequency domain and the timing between successive echoes is used to reconstruct the decay time of the FID signal and the maximum magnitude of the signal, both of which correspond to the hydration state of the tissue under sample.

Some embodiments configured to perform hydration monitoring employ a data processing technique called the "Null method," which works by pre-calibrating the systems power and pulse width to a certain volume of sample. With a posteriori knowledge of the power/pulse width required to create a null signal in the time domain the volume of water can be determined based on the same factory calibration of the device that associated said power/pulse width with a particular volume of sample. In effect, this method works by nulling or eliminating the signal with a particular power setting and assigning a quantitative number to hydration based on the power used to suppress the signal. Note that the signal is suppressed by delivering sufficient energy via the NMR transceiver coil to rotate the sample magnetization vector precisely 180° during the first half portion (0° to 180°) of the Rabi oscillation, such that no xy-plane (i.e., transverse) magnetization remains.

Square RF pulses are commonly used in most NMR experiments, as they are fairly straight forward to generate with a pulse generator. However, square pulses are not optimized for the sample geometry. Unsymmetrical sample geometry or variations in tissue can introduce inhomogeneities to the $B_0$ field when said sample is present. In some embodiments, a shaped (non-square) pulse is iteratively designed to optimize line shape and SNR. In some embodiments, a numerical method driven optimization routine is used to identify an appropriate shaped pulse. Based on an accumulated data set of shaped pulses corresponding to sample geometry (e.g., optically recorded), some embodiments employ a machine learning routine to identify the optimum pulse shape for an arbitrary sample geometry.

Data Processing

In the instance where frequency domain information is generated, reference deconvolution may be used in some embodiments to improve line shapes. Because the frequency domain consists of a single singlet peak, the water peak is self-referenced. The NMR data is re-convoluted with a stored Lorentzian signal to generate an ideal line shape.

Some embodiments are configured to use exponential filtering to improve SNR. In exponential filtering, the FID is multiplied by an exponential with the same decay time constant.

Some embodiments fit time domain data with an exponentially decaying function defined by two variables representing the relaxation time. The two variables are uniquely associated with the fundamental properties of the sample. For instance, any tissue or bone will have a unique set of relaxation times. The multi-exponential relaxation time models have the form:

$$M_z(t) = \sum_{i=1}^{n} M_{z,n}^0 \left(1 - e^{-t/T_{1,n}}\right)$$

and $$M_{xy}(t) = \sum_{i=1}^{n} M_{xy,n}^0 \left(e^{-t/T_{2,n}}\right)$$

where M represents the magnetization magnitude or signal.

After modeling the acquired data with the above multi-exponential model, a series of transverse relaxation time ($T_2$) are derived that correspond to the various tissue compositions in the sample. While the relaxation time from water is constant by itself, the removal of water from body material means that the aggregate relaxation time of the sample will start to increase as a result of decreased contribution of water which has a longer relaxation time than tissue or semi-solids. Therefore, the effective relaxation time will increase as water is removed from the body. Thus, $T_2$ can be an effective measurement parameter correlated to dehydration.

Figure 9:
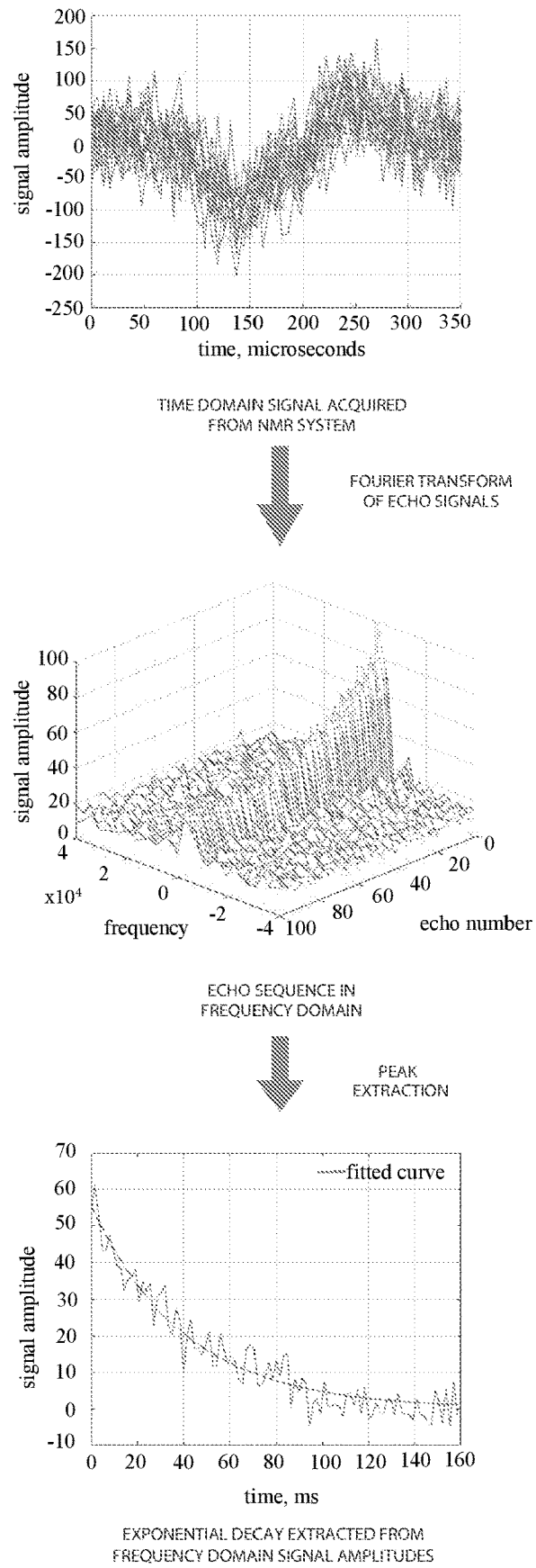
FIG. 9 illustrates a technique for FFT-based relaxation parameter modeling in accordance with some embodiments.

In some embodiments, relaxation parameters are computed automatically using models describing the time domain or frequency domain data. FIG. 9 shows an example of an exponential regression relaxation modeling technique that may be used in accordance with some embodiments.

Another technique that may be used to determine $T_2$ relaxation time from the frequency spectrum is by using the following formula:

$$T_2 = \frac{1}{\lambda}$$

where $\lambda$ is the coherence decay rate constant and is equivalent to half the frequency line width at half height of the FFT FID (i.e. frequency spectra).

Therefore, the relaxation time from a single spectrum can be obtained by knowing the line width of the spectral peak. The hydration state can from this point be obtained from a similar method described above for exponential modeling.

Another technique for determining the hydration state of a subject from the FID data recorded in accordance with some embodiments is to use a scalar value associated with the peak intensity (in either time or frequency domain), peak half height (in either time or frequency domain), or the area under the curve (in either time or frequency domains). Similar to how the intensity is gathered from $T_2$, other relaxation constants can be used to evaluate the hydration state of an individual. For instance, $T_1$, $T_{1\rho}$, or $T_{2*}$.

Instead of fitting the detected time-domain signal with bi-exponential or other model functions, distributions of relaxation times or diffusion coefficients can be derived by algorithms reminiscent of Laplace inversion. Laplace NMR can be used to remove ambiguity from signal overlap in 1 D distributions.

Example Applications

As discussed above, an application for an NMR monitoring device designed in accordance with the techniques described herein is as a hydration monitor. Some embodiments provide a method to detect in vivo states of hydration (e.g. water volume), which include: dehydration (hypohydration), euhydration, and hyperhydration. In such an application, an NMR FID signal may be recorded from any one or more of interstitial, intracellular, extracellular, and vascular tissue inside the sensitive volume of the transceiver induction coil. The transceiver can be used to perform single-voxel spectroscopy, multi-voxel spectroscopy, or magnetic resonance spectroscopy. Changes to hydration state can have a profound impact on human health, both physical and cognitive. The information about a subject's hydration state may be used by the subject to improve their health.

By collecting time-stamped hydration states, the device can also provide in vivo hydration monitoring (e.g., self-referenced changes in hydration state). Hydration monitoring may be either relative, with the sample signal being self-referenced to previously collected data, or quantitative monitoring, where the sample signal is referenced to a quantified signal. In the former case, the measurement is not absolute and requires collection of at least one other spectra before self-reference is possible. Applications of this general framework are diverse and include, but are not limited to:

Congestive heart failure home preventative care monitoring—Patients diagnosed with congestive heart failure often become hyperhydrated; this is also known as congestion. Congestion can lead to organ decompensation, which requires hospitalization. Care providers currently rely on patients to self-diagnose signs of congestion, such as weight changes, and admit themselves to the hospital emergency services. With inaccurate monitoring technology, false-positive admissions are commonplace. Home hydration state monitoring allows patients to identify pre-clinical congestion and self-regulate their fluid or salt ingestion in response.

Patient vital sign measurement—Quantified hydration state could be recorded during patient processing, along with other common vital sign information (e.g., heart rate, blood pressure, temperature, and survey symptom status), to give care providers a greater assessment of a patient's health.

Clinical applications for detecting hydration imbalances—Knowledge of hydration state (as it relates to hydration imbalance) is important for the diagnosis and treatment of patients with a range of disease types—particularly, chronic diseases. Examples include: diabetes, renal failure, congestive heart failure (described above), liver failure/cirrhosis, nephrolithiasis, nephrotic syndrome, brain swelling, colitis, cholera, water intoxication, hypernatremia, and cryptosporidium infection.

Fetal and maternal health monitoring—Monitoring of fetal and maternal hydration health during pregnancy may result in better mother/child outcomes.

Geriatric health monitoring—The elderly and seniors are particularly susceptible to severe dehydration, requiring hospitalization. Hydration state check-ups may reduce heatstroke related hospitalizations among the elderly population.

Method for determining intravascular volume status—The intravascular volume, which is comprised of blood plasma, is related to the hydration state of an individual. Assuming the patient is healthy and no water is lost to the surrounding tissue, the information recorded with in vivo NMR can be used as a proxy for intravascular volume status. To detect the volume of either the intravascular or the extravascular tissue, the device must be sensitive enough to distinguish relaxometry rates from each tissue type. This is often done with MRI, but is more difficult with a comparatively inhomogeneous magnet. Successful detection of changes in intravascular/extravascular volume may be used to identify changes in oncotic pressure, which is often related to disease state.

Cognitive performance assessment—Hydration state can be used to determine a person's cognitive acuity. For example, occupations that require the operation of heavy equipment (e.g., truck drivers, construction workers, pilots, bus drivers, etc.) could improve work place safety by monitoring for fatigue associated with hydration state. Battlefield situational awareness is another possible application of this technology. Soldiers operating in the field could use hydration state information to optimize their cognitive health. Another example could be corporations that could use hydration state information to improve employee performance and productivity.

Physical performance assessment—Studies suggest a strong connection between physical performance and hydration state. With this in mind, monitoring hydration state could be useful for any activity involving athletic performance such as distance running, team sports, or even warfare.

Monitoring of patients in clinical trials—Pharmaceutical companies have a financial interest in side effects associated with their therapeutic drug treatments. Hydration state information is not currently a robustly captured metric in clinical trials; thus, recording hydration state information could provide a more complete picture of patient health related to a therapeutic treatment.

Figure 10:
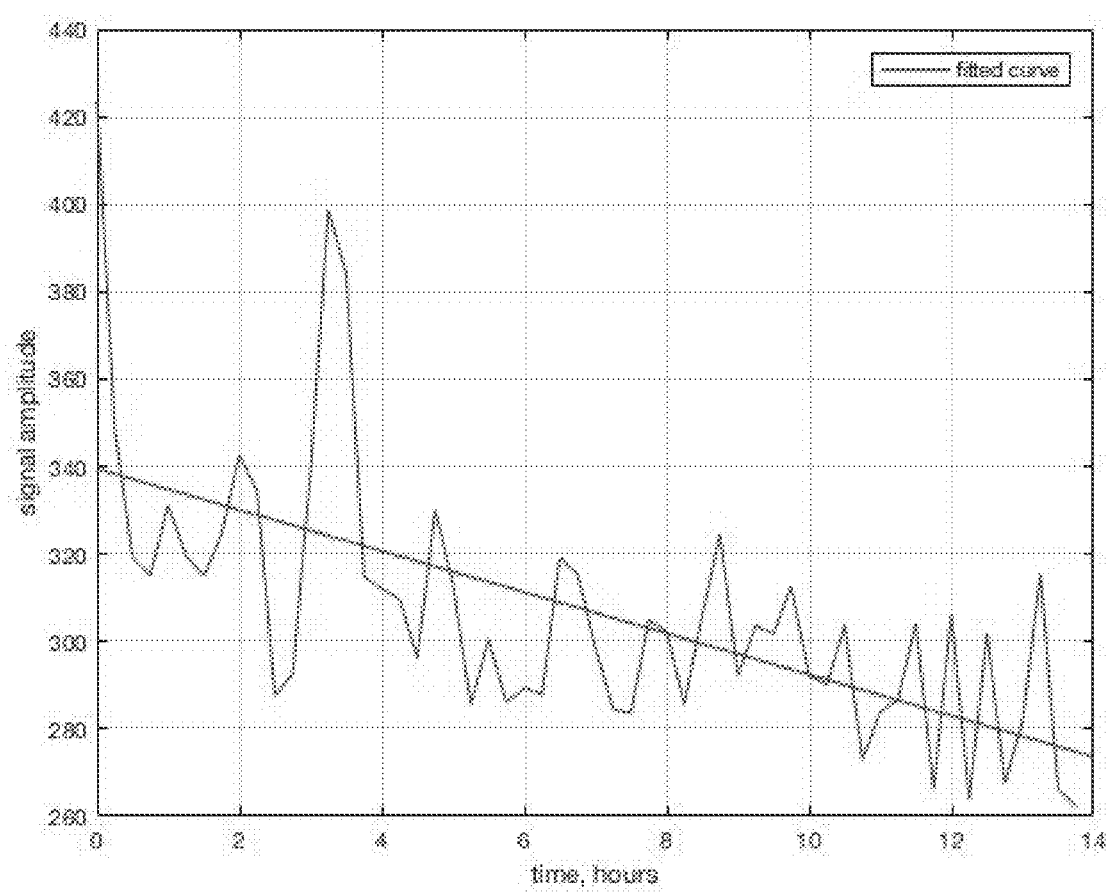
FIG. 10 illustrates a graph displaying results of a trend monitoring experiment collected using an NMR monitoring device designed in accordance with some embodiments.

A prototype of an NMR monitoring system designed in accordance with some embodiments was used to test the progressive dehydration over time of a non-biological sample, a dense piece of cotton fiber saturated with water, approximately 0.5 ml in volume. This sample was allowed to dry in open room temperature conditions over a period of hours, with measurements from the NMR system being taken every 15 minutes. FIG. 10 shows a trend was observed in dehydration commensurate with water evaporation from the sample over time.

As discussed above, some embodiments are configured to measure a subject's metabolism, with water being an example of a particular metabolite that may be measured. Metabolism is defined as the chemical transformations within cells that sustain life. The human metabolism is responsible for converting food to energy for cellular processes; breaking food into chemical building blocks for use by proteins, nucleic acids, lipids and carbohydrates; and eliminating/removing nitrogenous wastes. Metabolic processes are basic and essential for living organisms, and it is often the case that changes in metabolic state are related changes in health. For instance, many diseases have been characterized according to changes in their afflicted host's metabolism. Changes in fitness level can also trigger changes in metabolism. In both above examples, the metabolic pathways associated with fitness level or a particular disease vary widely and involve distinct metabolites. Water plays a role in many metabolic pathways, making it difficult when considered in isolation to yield insights about a particular condition. The primary purpose of recording metabolic information from water is to determine the fitness level of the monitored subject. To a lesser degree there may be some non-specific insight that can be gained about a subject's health from changes in hydration metabolic information.

Example Device Form Factors

Figure 11:
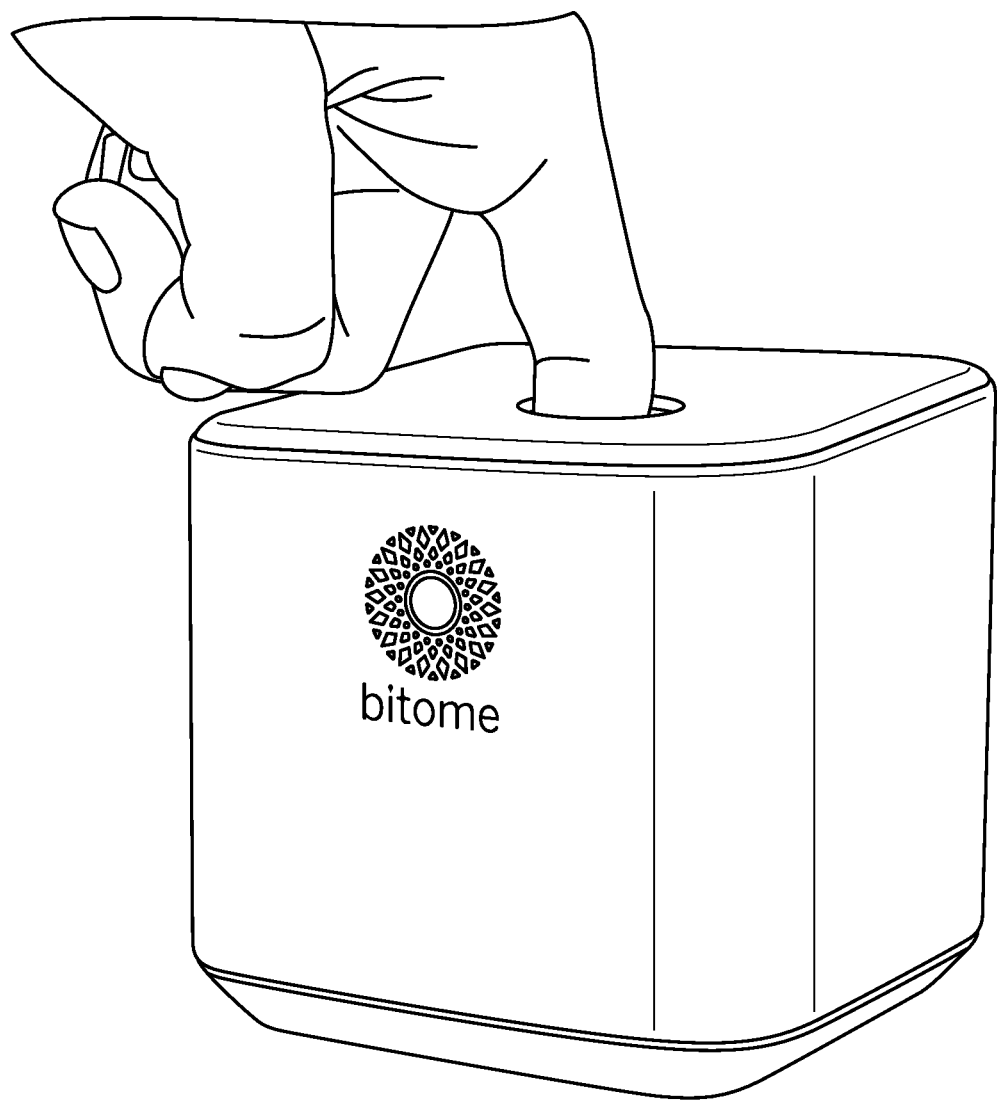
FIG. 11 illustrates an NMR monitoring device in accordance with some embodiments, in which a metabolic state of a subject is assessed based on a measurement using the subject's finger.

FIG. 11 illustrates a form factor for an in vivo NMR device in accordance with some embodiments. The device is configured to perform an NMR relaxometry experiment to measure a subject's hydration state using a finger (or thumb) measurement. A spectrometer, solenoid coil, Halbach magnet array, and shielding case are combined together in a single enclosure. In this design, a subject may insert a finger into the bore of the Halbach magnet array by pressing down a long track button which conceals the opening. Once the finger is pushed down into the center of the pickup coil/magnet, a switch/sensor at the bottom of the magnet may be activated to initiate the measurement routine. The case can be equipped with LED lights for indicating experiment status. The device can also be equipped with a screen or finger print scanner. The finger insert may be tapered to keep the subject's finger centered within the magnetic field and sensitive volume of the transceiver induction coil.

An alternative layout for the hydration monitoring station may be used, for example, by sports teams as a sideline hydration status station or by gyms as a check-in booth for patrons. A team sports hydration status station may be outfitted with a finger print scanner to identify individual athletes and associate the recorded hydration state data with their profile. Information may be forwarded to the team coach. In the application of a device for gyms, an RFID tag reader may be included such that the patron's hydration state is logged simultaneously while checking them into the gym. Information could be used by personal trainers to customize workout routines.

Figure 12:
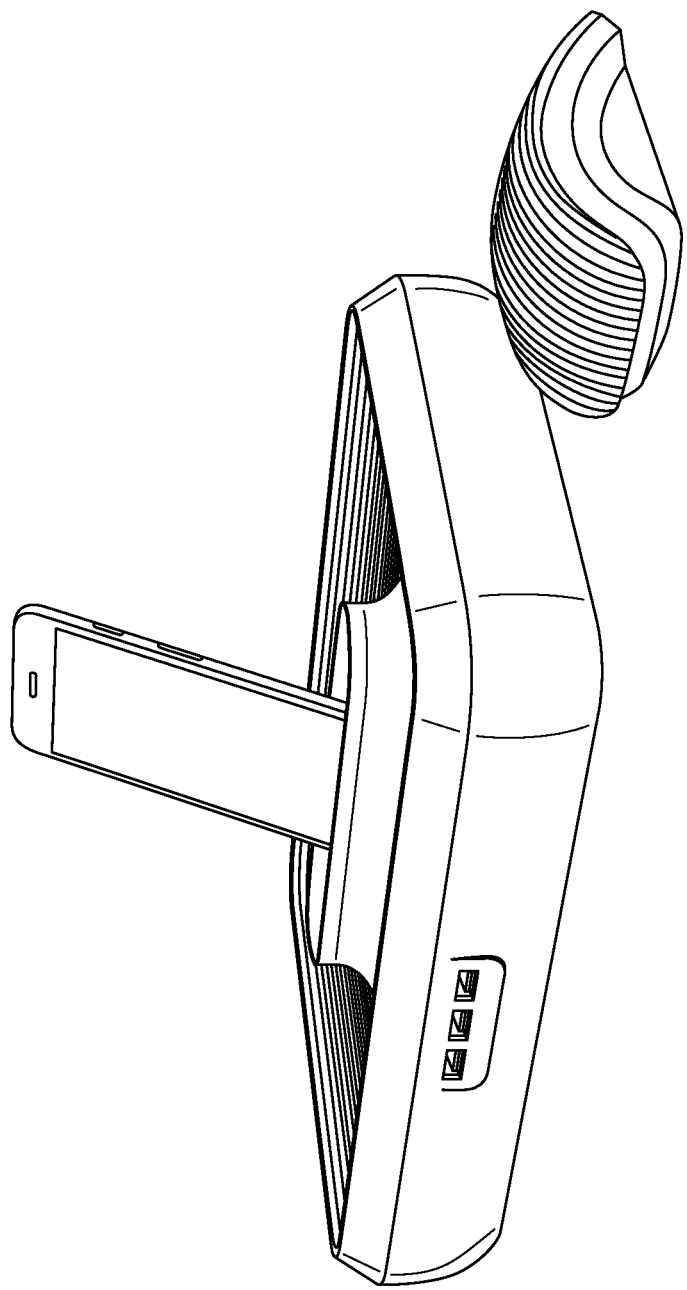
FIG. 12 illustrates an alternate NMR monitoring device integrated with a computer mouse in accordance with some embodiments.

FIG. 12 shows an embodiment in which a computer mouse is integrated with a built-in one-sided magnet arrangement and transceiver coil used to record hydration state measurements from the palm of the subject's hand. In an alternate embodiment, the spectrometer can also be located in the body of the mouse.

Figure 13:
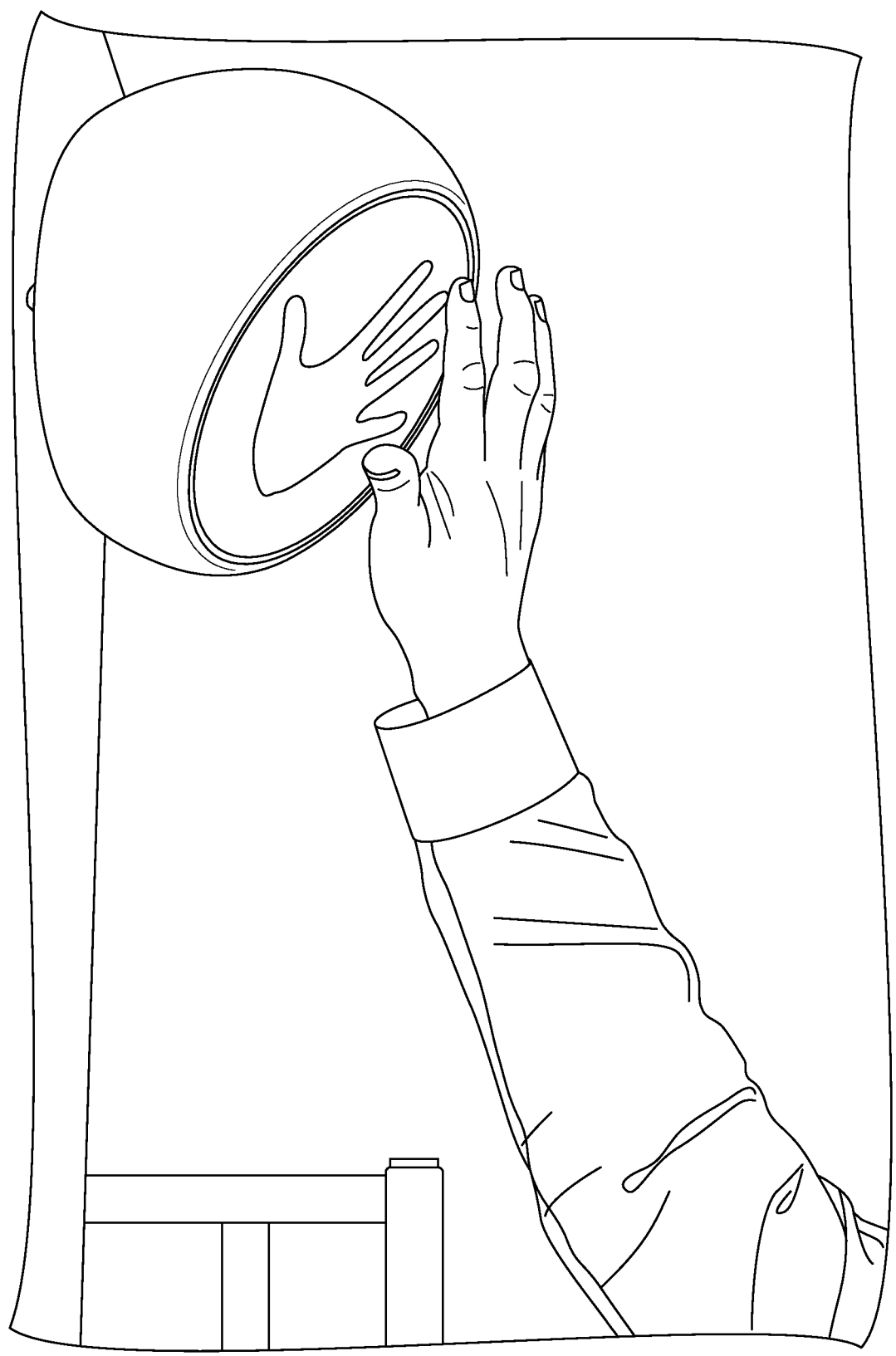
FIG. 13 illustrates an alternate NMR monitoring device in accordance with some embodiments, in which a metabolic state of a subject is assessed based on a measurement using the subject's hand.

FIG. 13 shows an embodiment including a one-sided magnet and planar transceiver coil used to record information from the subject's entire hand. In some embodiments, the one-sided magnet may be configured to rotate to improve line shape.

Figure 14:
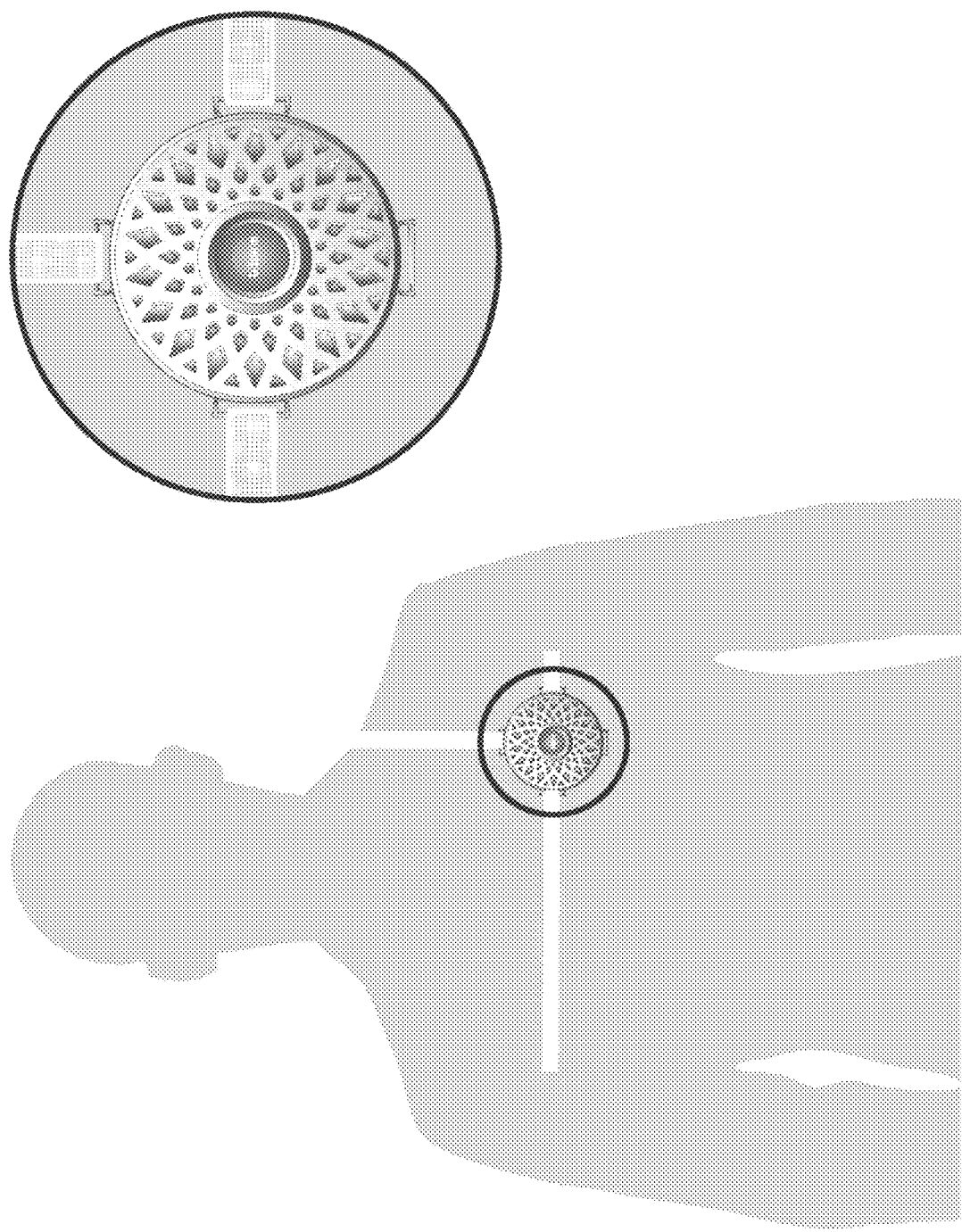
FIG. 14 illustrates a wearable NMR monitoring device in accordance with some embodiments.

FIG. 14 shows a conceptual image of a chest-mounted one-sided NMR device in accordance with some embodiments. In this implementation, the spectrometer and power source may also be located on board the device in a single shielded case. Continuous hydration state monitoring is possible in this form factor. The collected information may be sent wirelessly (e.g., via Bluetooth) to a mobile device or desktop connected dongle when in range. Additionally, or alternatively, the data may be stored locally on the device. Example users of the device may include, but is not limited to, athletes, consumers interested in quantified self, employees, and patients in a clinical setting. In some instantiations, indicator lights may adorn the exterior of the device and display the subject's hydration state. All data may be collected and presented to the user via the companion software application.

In another embodiment, the NMR monitoring device is configured to monitor one or more metabolites by being attached to the thigh, ankle, or wrist of a subject in the form of a watch or band.

Some embodiments may include a user interface for an application locally installed on an electronic device (e.g., a mobile phone) that may be used to display hydration information to a user in accordance with some embodiments. As discussed above, data collected on the physical sensor may be stored locally before being transmitted (wired or wirelessly) to a computer (either mobile or desktop). Once synced to a computer, the information can then be sent to a server for processing, and at least some information from the server is returned to the application for display. Alternatively, the information synced to the computer may be retained and processed locally when necessary (such as during an emergency or when network connectivity is unavailable). In some embodiments, the processed information is presented as a chart in a continuous measurement mode or as a standalone value approximating the hydration state of the individual. Recommendations for fluid and salt intake may be adjusted based on the collected data and body type of the user.

In accordance with some embodiments, an application executing on a computer may be configured to interact with an electronic device of a care provider. For example, patient information may be shared with the hospital and doctor overseeing the treatment of the patient. The care provider may have the ability to make suggestions or provide feedback to the patient via the in-software communication feature. Patients may also use the communication feature to ask questions, receive feedback, and otherwise communicate with the care provider representative.

Some embodiments apply a predictive analytics routine to the accumulated data set and a risk factor associated with a subject's likelihood to need medical attention may be determined and output.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, a tape, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A nuclear magnetic resonance (NMR) monitoring device, comprising:
    at least one magnet configured to generate a primary magnetic field;
    a transceiver coil arranged within the primary magnetic field, wherein the transceiver coil is configured to apply a time series of radiofrequency (RF) pulses to a sample located within the primary magnetic field and to detect an NMR signal generated in response to application of the time series of RF pulses;
    a tuning circuit coupled to the transceiver coil, wherein the tuning circuit automatically adjusts a resonant frequency of the transceiver coil to a frequency associated with the primary magnetic field based on a dynamically determined transmitted signal, wherein the dynamically determined transmitted signal is different from the time series of RF pulses; and
    an NMR spectrometer having a software defined radio (SDR) architecture, wherein the NMR spectrometer is communicatively coupled to the transceiver coil, wherein the NMR spectrometer comprises:
        digital pulse generation circuitry configured to generate a digital representation of the time series of RF pulses;
        a digital-to-analog converter configured to convert the digital representation of the time series of RF pulses to an analog signal provided to the transceiver coil;
        an analog-to-digital converter configured to convert the detected NMR signal to a digital signal; and
        digital receive circuitry configured to process the digital signal to determine at least one metabolic state of the sample;
    at least one field sensor configured to measure at least one property of the primary magnetic field;
    at least one microcontroller unit configured to determine the frequency associated with the primary magnetic field based, at least in part, on the at least one measured property of the primary magnetic field and stored values; and
    wherein the tuning circuit comprises at least one digitally-tunable component arranged in series with the transceiver coil, and wherein the microcontroller unit is further configured to adjust a value of the at least one digitally-tunable component based, at least in part, on the determined frequency associated with the primary magnetic field.

2. The NMR monitoring device of claim 1, wherein the digital receive circuitry is configured to perform quadrature detection and bandpass filtering.

3. The NMR monitoring device of claim 1, wherein the analog-to-digital converter is configured to convert the detected NMR signal to the digital signal without first downconverting the detected NMR signal to baseband.

4. The NMR monitoring device of claim 1, further comprising: wherein the NMR spectrometer is further configured to adjust, during operation of the NMR monitoring device, a frequency of the RF pulses in the time series of RF pulses based on the frequency associated with the primary magnetic field.

5. The NMR monitoring device of claim 1, wherein the at least one magnet comprises a plurality of permanent magnets arranged in a Halbach configuration.

6. The NMR monitoring device of claim 1, further comprising a shielding structure arranged between the sample within the primary magnetic field and the transceiver coil, wherein the shielding structure is configured to electrically decouple the sample from the transceiver coil.

7. The NMR monitoring device of claim 6, wherein the shielding structure comprises a grating of conductive material.

8. The NMR monitoring device of claim 1, wherein the at least one field sensor comprises a temperature sensor and/or a magnetometer.

9. The NMR monitoring device of claim 1, further comprising:
    at least one shim coil configured to compensate for inhomogeneities in the primary magnetic field when a current flows through the at least one shim coil; and
    a feedback loop shim controller configured to automatically adjust a value of the current flowing through the at least one shim coil during operation of the NMR monitoring device.

10. The NMR monitoring device of claim 9, wherein the value of the current is automatically adjusted based, at least in part, on an intensity of the detected NMR signal.

11. The NMR monitoring device of claim 9, wherein the value of the current is automatically adjusted based, at least in part, on data received from at least one field sensor arranged within the primary magnetic field.

12. The NMR monitoring device of claim 1, further comprising a transmitter coil arranged near the transceiver coil to generate the dynamically determined transmitted signal, wherein the transceiver coil when operating in receive mode is configured to detect the dynamically determined transmitted signal from the transmitter coil in addition to the detected NMR signal,
    wherein the spectrometer is configured to quantify the detected NMR signal based, at least in part, on the detected dynamically determined transmitted signal from the transmitter coil.

13. The NMR monitoring device of claim 1, wherein determining the metabolic state of the sample comprises determining a hydration state of the sample.

14. A method of monitoring a metabolic rate of a sample using a nuclear magnetic resonance (NMR) monitoring device, comprising:
    generating a primary magnetic field via at least one magnet;
    arranging a transceiver coil within the primary magnetic field, wherein the transceiver coil is configured to apply a time series of radiofrequency (RF) pulses to a sample located within the primary magnetic field and to detect an NMR signal generated in response to application of the time series of RF pulses;
    coupling a tuning circuit to the transceiver coil, wherein the tuning circuit automatically adjusts a resonant frequency of the transceiver coil to a frequency associated with the primary magnetic field based on a dynamically determined transmitted signal, wherein the dynamically determined transmitted signal is different from the time series of RF pulses; and communicatively coupling an NMR spectrometer having a software defined radio (SCR) architecture to the transceiver coil, where the NMR spectrometer comprises:
  generating a digital representation of the time series of RF pulses with digital pulse generation circuitry;
  converting the digital representation of the time series of RF pulses to an analog signal provided to the transceiver coil using a digital-to-analog converter;
  convert the detected NMR signal to a digital signal with an analog-to-digital converter; and
  processing the digital signal to determine at least one metabolic state of the sample using digital receive circuitry;
measuring at least one property of the primary magnetic field with at least one field sensor;
determining, with at least one microcontroller unit, the frequency associated with the primary magnetic field based, at least in part, on the at least one measured property of the primary magnetic field and stored values; and
wherein the tuning circuit comprises at least one digitally-tunable component arranged in series with the transceiver coil, and wherein the microcontroller unit is further configured to adjust a value of the at least one digitally-tunable component based, at least in part, on the determined frequency associated with the primary magnetic field.

15. The method of monitoring a metabolic rate of a sample of claim 14, further comprising:
configuring the digital receive circuitry to perform quadrature detection and bandpass filtering.

16. The method of monitoring a metabolic rate of a sample of claim 14, further comprising:
converting, with the analog-to-digital converter, the detected NMR signal to the digital signal without first downconverting the detected NMR signal to baseband.

17. The method of monitoring a metabolic rate of a sample of claim 14, further comprising:
adjusting with the NMR spectrometer, during operation of the NMR monitoring device, a frequency of the RF pulses in the time series of RF pulses based on the frequency associated with the primary magnetic field.

18. The method of monitoring a metabolic rate of a sample of claim 14, wherein the at least one magnet comprises a plurality of permanent magnets arranged in a Hallbach configuration.

19. The method of monitoring a metabolic rate of a sample of claim 14, further comprising:
electrically decoupling the sample from the transceiver coil by arranging a shielding structure between the sample within the primary magnetic field and the transceiver coil.

20. The method of monitoring a metabolic rate of a sample of claim 19, wherein the shielding structure comprises a grating of conductive material.

21. The method of monitoring a metabolic rate of a sample of claim 14, wherein the at least one field sensor comprises a temperature sensor and/or a magnetometer.

22. The method of monitoring a metabolic rate of a sample of claim 14, further comprising:
compensating, using at least one shim coil, for inhomogeneities in the primary magnetic field when a current flows through the at least one shim coil; and
automatically adjusting, using a feedback loop shim controller, a value of the current flowing through the at least one shim coil during operation of the NMR monitoring device.

23. The method of monitoring a metabolic rate of a sample of claim 22, further comprising:
automatically adjusting the value of the current based, at least in part, on an intensity of the detected NMR signal.

24. The method of monitoring a metabolic rate of a sample of claim 22, further comprising:
automatically adjusting the value of the current based, at least in part, on data received from at least one field sensor arranged within the primary magnetic field.

25. The method of monitoring a metabolic rate of a sample of claim 14, further comprising:
generating the dynamically determined transmitted signal based on a transmitter coil arranged near the transceiver coil, wherein the transceiver coil when operating in receive mode is configured to detect the dynamically determined transmitted signal from the transmitter coil in addition to the detected NMR signal; and
quantifying, using the spectrometer, the detected NMR signal based, at least in part, on the detected dynamically determined transmitted signal from the transmitter coil.

26. The method of monitoring a metabolic rate of a sample of claim 14, further comprising:
determining the metabolic state of the sample by determining a hydration state of the sample.

* * * * *

UNITED STATES PATENT AND TRADEMARK OFFICE
CERTIFICATE OF CORRECTION

PATENT NO. : 11,439,313 B2  
APPLICATION NO. : 15/597053  
DATED : September 13, 2022  
INVENTOR(S) : Herbert B. Ryan et al.

It is certified that error appears in the above-identified patent and that said Letters Patent is hereby corrected as shown below:

On the Title Page

At item (73) 'Assignee' please replace: "Bitome, Inc., Boston, MA (US)" with --Ginkgo Bioworks, Inc., Boston, MA (US)--.

Signed and Sealed this  
Twenty-seventh Day of September, 2022

Katherine Kelly Vidal  
*Director of the United States Patent and Trademark Office*